(12) United States Patent
Samuilov et al.

(10) Patent No.: US 10,101,219 B2
(45) Date of Patent: Oct. 16, 2018

(54) CARBON NANOTUBE SENSING SYSTEM, CARBON NANOTUBE DEW POINT HYGROMETER, METHOD OF USE THEREOF AND METHOD OF FORMING A CARBON NANOTUBE DEW POINT HYGROMETER

(71) Applicants: THE RESEARCH FOUNDATION FOR THE STATE UNIVERSITY OF NEW YORK, Albany, NY (US); COSA XENTAUR, Yaphank, NY (US)

(72) Inventors: Vladimir Samuilov, Sound Beach, NY (US); John Lewis Ayres, Manorville, NY (US)

(73) Assignees: The Research Foundation for The State University of New York, Albany, NY (US); Cosa Xentaur, Yaphank, NY (US)

( * ) Notice: Subject to any disclaimer, the term of this patent is extended or adjusted under 35 U.S.C. 154(b) by 494 days.

(21) Appl. No.: 14/632,540

(22) Filed: Feb. 26, 2015

(65) Prior Publication Data
US 2015/0233856 A1   Aug. 20, 2015

Related U.S. Application Data

(63) Continuation-in-part of application No. 13/062,658, filed as application No. PCT/US2009/056273 on Sep. 8, 2009, now Pat. No. 9,086,363.
(Continued)

(51) Int. Cl.
| G01N 27/04 | (2006.01) |
| G01K 13/00 | (2006.01) |
| G01N 27/12 | (2006.01) |

(52) U.S. Cl.
CPC ............ *G01K 13/00* (2013.01); *G01N 27/121* (2013.01); *G01N 27/127* (2013.01)

(58) Field of Classification Search
CPC ..... G01K 13/00; G01N 27/121; G01N 27/127
(Continued)

(56) References Cited

U.S. PATENT DOCUMENTS

| 4,740,664 A | 4/1988 | Payne et al. | |
| 5,364,185 A * | 11/1994 | VanZandt | G01N 25/68 |
| | | | 374/28 |

(Continued)

FOREIGN PATENT DOCUMENTS

| EP | 0 768 527 A2 | 4/1997 |
| JP | 2005070038 | 3/2005 |

(Continued)

OTHER PUBLICATIONS

Ma, Xingfa, et al, Gas Sensing Behavior of Nano-Structured Polypyrrole Prepared by "Carbon Nanotubes Seeding" Approach, Journal of Nanoparticle Reaearch, Feb. 2008, vol. 10 No. 2, pp. 289-296.
(Continued)

*Primary Examiner* — Natalie Huls
*Assistant Examiner* — Monica S Young
(74) *Attorney, Agent, or Firm* — Scully, Scott, Murphy & Presser, P.C.

(57) ABSTRACT

A system, a method of use, and a Carbon Nanotube (CNT) condensation sensor for determining a dew point and/or ice point is provided. For example, a sensing system may include a thermal device configured to generate heating or cooling to change a temperature of a surface, a temperature sensor for measuring the temperature of the surface, a controller configured to control the thermal device, a carbon nanotube (CNT) condensation sensor mounted on the surface having a moisture sensitive resistance and a processor
(Continued)

configured to determine one or more parameters based on the moisture sensitive resistance of the CNT condensation sensor and the temperature measured by the temperature sensor. The one or more parameter can be used to determine the dew point and/or ice point. A method for forming a carbon nanotube (CNT) condensation sensor is also provided.

28 Claims, 24 Drawing Sheets

Related U.S. Application Data

(60) Provisional application No. 61/094,444, filed on Sep. 5, 2008, provisional application No. 61/946,023, filed on Feb. 28, 2014.

(58) Field of Classification Search
USPC .................................................. 73/29.05
See application file for complete search history.

(56) References Cited

U.S. PATENT DOCUMENTS

| | | | | |
|---|---|---|---|---|
| 5,619,144 | A * | 4/1997 | Stormbom | G01N 27/18 |
| | | | | 324/441 |
| 2,966,939 | A | 10/1999 | Tauchi | |
| 6,022,138 | A * | 2/2000 | Sonander | G01N 25/68 |
| | | | | 374/28 |
| 6,276,202 | B1 | 8/2001 | Latarius | |
| 6,865,940 | B2 | 3/2005 | Poole | |
| 8,915,121 | B2 * | 12/2014 | Kumar | B82Y 20/00 |
| | | | | 73/29.01 |
| 2002/0040598 | A1 * | 4/2002 | Sugaya | G01N 27/121 |
| | | | | 73/335.02 |
| 2004/0135684 | A1 | 7/2004 | Steinthal et al. | |
| 2005/0036905 | A1 | 2/2005 | Gokturk | |
| 2005/0081625 | A1 * | 4/2005 | Chen | B82Y 30/00 |
| | | | | 73/335.02 |
| 2008/0142866 | A1 | 6/2008 | Choi et al. | |
| 2010/0089772 | A1 * | 4/2010 | Deshusses | G01N 27/127 |
| | | | | 205/781 |
| 2010/0116666 | A1 | 5/2010 | Park et al. | |
| 2011/0024409 | A1 | 2/2011 | Shah et al. | |
| 2011/0167894 | A1 | 7/2011 | Samuilov | |
| 2013/0180330 | A1 | 7/2013 | Gao et al. | |
| 2014/0182372 | A1 * | 7/2014 | Scott | G01N 27/121 |
| | | | | 73/335.05 |
| 2014/0283630 | A1 * | 9/2014 | Mourey | G01D 11/00 |
| | | | | 73/865.8 |
| 2017/0138922 | A1 * | 5/2017 | Potyrailo | G01N 33/2888 |

FOREIGN PATENT DOCUMENTS

| | | | | |
|---|---|---|---|---|
| KR | 1020060070672 | | 6/2006 | |
| KR | 1020070112657 | | 11/2007 | |
| KR | 2012-000218 A | | 9/2012 | |
| WO | 2013/043148 | | 3/2013 | |
| WO | WO 2013043148 A1 * | | 3/2013 | ........... G01N 27/121 |
| WO | WO 2013060767 A2 * | | 5/2013 | ........... C08G 18/289 |
| WO | WO 2014043508 A1 * | | 3/2014 | ............. G01N 25/20 |

OTHER PUBLICATIONS

PCT/ISAI237 Written Opinion issued on PCT/US2009/056273.
PCT/ISAI210 Search Report issued on PCT/US2009/056273.
Thomas, Dan, Aerosonde Robotic Aircraft, Barrow Aug. 2000, Operation: Icing Sensor Data Report, Sep. 21, 2000.
LPDT User's Manual, LDO.01.D/200D Rev.D Jun. 1, 1999, Xentaur Corporation.
International Search Report and Written Opinion dated Jul. 8, 2015.

* cited by examiner

CARBON NANOTUBE SENSING SYSTEM, CARBON NANOTUBE DEW POINT HYGROMETER, METHOD OF USE THEREOF AND METHOD OF FORMING A CARBON NANOTUBE DEW POINT HYGROMETER

RELATED APPLICATIONS

This application is a continuation-in part application of U.S. application Ser. No. 13/062,658 filed Mar. 7, 2011, which is a national phase application of PCT/US2009/056273 filed Sep. 8, 2009, which claims the benefit of and priority to U.S. Provisional Application No. 61/094,444, filed Sep. 5, 2008, the entirety of which are incorporated by reference.

This application also claims the benefit of and priority to U.S. Provisional Application No. 61/946,023 filed Feb. 28, 2014, the entirety of which is incorporated by reference.

FIELD OF THE DISCLOSURE

The present disclosure relates generally to moisture sensing systems, and methods of operation thereof. More particularly, the present disclosure relates to carbon nanotube sensors for repeatedly detecting absolute humidity in terms of dew and/or frost point or relative humidity, a method of using the same in a sensing system, a method of manufacturing carbon nanotube sensor(s) and a carbon nanotube sensor.

BACKGROUND

Conventional moisture sensing systems include a Loop Powered Dewpoint Transmitter (LPDT), such as the hyper thin film HTF™ Al$_2$O sensor provided by Xentaur Corporation. The LPDT system allows a user to view dewpoint by monitoring the operation of a sensor constructed as a capacitor having a dielectric that consists of porous aluminum oxide, as well as monitoring the gas that enters pores of the aluminum oxide. The capacitor plates, i.e. electrodes, are an aluminum substrate and a porous gold layer deposited on top of the aluminum oxide, and the electrode having the porous gold layer allows transfer of gases into or out of the aluminum oxide pores. The capacitance due to the aluminum oxide is constant, while the capacitance due to the adsorption of water on the surface of the aluminum oxide dielectric will vary according to the water vapor content and pressure. Since the dielectric constant of adsorbed water is orders of magnitude larger than the dielectric constant of any gas that might be adsorbed and measured, the quantity of water vapor present in the pores resulting in water adsorption on the dielectric will change the capacitance of the sensor to a much greater extent than other variables.

However, the use of an LPDT sensor will often cause pore volume to change due to contaminant clogging, residual oxidation, metal migration etc. Thus, re-calibration of the sensor is needed.

SUMMARY

Disclosed is a system for determining a dew point and/or frost point from a measurement of an inflection point and/or ice point. The system includes a thermal device configured to heat or cool a temperature controlled surface.

The system also includes a temperature sensor for measuring a temperature of the temperature controlled surface. The temperature sensor may be mounted to the temperature controlled surface or placed adjacent to the temperature controlled surface.

The system also includes a carbon nanotube (CNT) condensation sensor. The CNT condensation sensor is mounted on the temperature controlled surface. While the temperature of the temperature controlled surface with the CNT condensation sensor decreases, the CNT condensation sensor exhibits moisture sensitive resistance change which responds to (i) the condensation of polar molecules during formation of liquid water; (ii) formation of liquid water followed by the formation of solid water (ice); and (iii) formation of liquid water and solid water; or (iv) direct formation of solid water.

The system may also include one or more controllers. The one or more controllers are configured to control the temperature of the temperature controlled surface (which the CNT condensation sensor is mounted to). For example, a first controller of the one or more controllers may be configured to reduce the temperature of the temperature controlled surface from an initial maximum temperature ($T_{high}$) degrees C., which is above the dew point ($T_{dew}$) degrees C. to a minimum temperature ($T_{low}$) degrees C. The first controller may control the temperature change over time to be fixed, e.g., fixed temperature scan rate of change. Alternatively, the first controller may control the temperature change over time to be variable, e.g., variable temperature scan rate. The scan rate is defined as $dT_{surface}/dt$ (degrees C./sec). The scan rate can be slow or fast.

A second controller may be configured to increase the temperature of the temperature controller surface from the minimum temperature to the maximum temperature in order to dry the surface and prepare the CNT condensation sensor for subsequent scans. The functionality of the first and second controllers may be integrated into a single controller.

The system may also include a signal conditioner to receive a signal from the CNT condensation sensor and the temperature sensor.

The system may also include a processor, such as a CPU, configured to determine the resistance of the CNT condensation sensor from an analog or digital output from the signal conditioner.

The processor may also analyze the resistance value over time to determine one or more parameters. The one or more parameter may include a temperature, a maximum resistance point with respect to temperature, a first derivative of resistance with respect to temperature and a second derivative of resistance with respect to temperature and evaluate the one or more parameters.

The first derivative is the CNT condensation sensor resistance ($R_{CNT}$) with respect to the temperature of the temperature controlled surface ($T_{surface}$), namely $dR_{cnt}/dT_{surface}$ (ohms/degree C.).

The second derivative is the change of slope of the CNT sensor resistance with respect to the temperature of the temperature controlled surface namely $dR_{cnt}^2/dT_{surface}^2$.

The processor may also be configured to determine an inflection point $T_{inflection}$ (degrees C.). $T_{inflection}$ corresponds to a point where the adsorbed water is at or approaches saturation of the adsorption site on the surface of the CNT condensation sensor. $T_{inflection}$ is based on one or more parameters of the measured resistance of the CNT condensation sensor with respect to the temperature of the temperature controlled surface.

$T_{inflection}$ can be determined by the following criteria: 1) the "slope" or "$1^{st}$ derivative $dR_{cnt}/dT_{surface}$" (ohms/° C.) is a minimum, 2) the "slope is negative" or "$1^{st}$ derivative $(dR_{cnt}/dT_{surface})<0$" for both $T>T_{inflection}$ and $T<T_{inflection}$, 3) the "change in slope" is zero at $T_{inflection}$ (° C.) or "$2^{nd}$ derivative $d^2R_{cnt}/dT^2_{surface}$" (ohms/° C./° C.)=0 at $T_{dew}$ (° C.), and 4) the "change in slope" or "$2^{nd}$ derivative $d^2R_{cnt}/dT^2_{surface}$" (ohms/° C./° C.) is positive (or >0) for surface temperatures $T_{surface}$ (° C.) above $T_{inflection}$ (° C.) and negative (or <0) for surface temperatures $T_{surface}$ (° C.) below $T_{inflection}$ (° C.).

The processor may also be configured to determine the ice point $T_{ice}$ (° C.). $T_{ice}$ is lower than inflection point $T_{inflection}$ (° C.). $T_{ice}$ is where condensed water is freezing and forming ice. $T_{ice}$ can be determined by the following criteria: 1) the "slope" is negative for temperatures above $T_{ice}$ (° C.)—the "$1^{st}$ derivative $dR_{cnt}/dT_{surface}$" (ohms/° C.)<0 for $T_{surface}$ (° C.)>$T_{ice}$ (° C.), 2) the "slope" is positive below $T_{ice}$ (° C.)—the "$1^{st}$ derivative $dR_{cnt}/dT_{surface}$" (ohms/° C.)>0 for T (° C.)<$T_{ice}$ (° C.), 3) the "$1^{st}$ derivative $dR_{cnt}/dT_{surface}$" is zero or undefined at the ice point $T_{ice}$ (° C.)—4) conditions 1-3 resulting in a maximum extremum or "peak" in the $R_{cnt}$ (ohms) versus $T_{surface}$ (° C.) curve where $T_{surface}$ (° C.) equals $T_{ice}$ (° C.), and 5) immediately following $T_{ice}$ (° C.), as the surface temperature is further decreased during the scan, the magnitude of the CNT resistance $R_{CNT}$ (ohms) drops off abruptly in magnitude providing the characteristic icing signature.

The processor may also be configured to determine a dew point $T_{dew}$(° C.). For dew points greater than 0° C., the processor can determine the dew point as follows: 1) for slow temperature scan rates $dT_{surface}/dt$ below ~0.1° C./sec, the inflection point $T_{inflection}$ (° C.) as described above is the dew point $T_{dew}$ (° C.) and 2) for faster scan rates above $dT_{surface}/dt$ ~0.1° C./sec other factors are considered. For example, fluid momentum, energy (thermal), and mass (diffusion) transfer limitations, in addition to adsorption and condensation kinetic limitations become important. Thus, the CNT resistance $R_{CNT}$ (ohms) versus surface temperature $T_{surface}$ (° C.) is shifted lower and becomes broader, and the inflection point $T_{inflection}$ (° C.) determines the dew point $T_{dew}$ (° C.) via empirical correlation for a fixed set of parameters such as flow rate, gas temperature and pressure, cell design, and temperature scan rate.

For dew points lower than 0° C., the processor can determine the dew point as follows: 1) for slow temperature scan rates $dT_{surface}/dt$ below ~0.1° C./sec, the ice point as described above is the "frost point" $T_{frost}$ (° C.) from which the dew point $T_{dew}$ may be calculated, and 2) for faster scan rates above $dT_{surface}/dt$ ~0.1° C./sec other factors are considered. For example, fluid momentum, energy (thermal), and mass (diffusion) transfer limitations, in addition to adsorption and condensation kinetic limitations become important. Thus, the ice point $T_{ice}$ (° C.) and/or the inflection point $T_{inflection}$ (° C.) which becomes discernable for fast scan rates allows the determination of the frost point $T_{frost}$ (° C.) and the dew point $T_{dew}$ (° C.) via empirical correlation for a fixed set of parameters such as flow rate, gas temperature and pressure, cell design, and temperature scan rate.

Also disclosed is a carbon nanotube (CNT) condensation sensor. The CNT condensation sensor can be comprised of single walled carbon nanotubes (SWCNTs), multi-walled carbon nanotubes (MWCNTs), graphene, graphene oxide, or other continuous 2-dimensional conjugated pi-bonded carbon network surface material. In as aspect of the disclosure, the CNT sensor is a multi-walled carbon nanotubes.

The CNT condensation sensor may be composed of a single carbon nanotube (CNT), several carbon nanotubes (CNTs), a random isotropic network of CNTs (random mat or film of CNT), an oriented anisotropic network of CNTs, or multiple of (CNTs) in an oriented bundle. In as aspect of the disclosure, the CNT condensation sensor is composed of at least one CNT randomly deposited as a film.

The CNT condensation sensor may be composed of carbon nanotubes (CNTs) 1 to 100 nanometer (nm) in diameter and 0.1 to 100 microns (μm) in length. In an aspect of the disclosure, the CNT consists of CNTs 10 to 20 nm in diameter and 1 to 10 μm in length.

In an aspect of the disclosure no addition of a secondary binder is used, rather utilizing the CNT defect structure itself as a binder and source of dangling carbon chains and moieties for binding along with chemical processing in which thermal and mechanical energy are provided as indicated.

Alternatively, in another aspect of the disclosure, the CNT condensation sensor composite can be made from CNTs and an appropriate binder such as a polymer including but not limited to polyethylene, polypropylene, polytetrafluoroethylene, epoxy, cyanoacrylate.

The CNT condensation sensor has a surface chemistry consisting of defects consisting of oxygenated functional surface groups containing, for example (but not limited to), one or more of the following polar carbon-oxygen groups: carboxyl and phenol (phenolic hydroxyl)

Alternatively, the CNT condensation sensor can have a surface chemistry consisting of oxygenated functional surface groups containing, for example (but not limited to), one or more of the following polar carbon-oxygen groups: carboxyl and phenol (phenolic hydroxyl), lactone, lactol, carbonyl, anhydride, ether, and quinine.

For example, the surface chemistry can consist of a mixture of carboxyl, phenolic hydroxyl, lactone, and lactol.

The CNT condensation sensor may be made by chemical oxidation and subsequent chemical, thermal, and mechanical processing. The process includes placing carbon nanotube(s) in an acid solution. In an aspect of the disclosure, the acid solution includes a 3:1 concentrated sulfuric acid to concentrated nitric acid solution. In another aspect of the disclosure the acid solution may include hydrogen peroxide, nitric acid, sulfuric acid/nitric acid mixture of 10:1 to 1:10 diluted or not diluted in water, or a permanganate oxidizing solution. The carbon nanotudes will exhibit defects in structure consisting of oxygenated functional surface groups arising due to the intrinsic processing of CNTs which come as received from a manufacturer and placing the carbon nanotubes in the acid solution.

Additionally, the process includes applying mechanical energy to the dispersion. The mechanical energy can be from mixing such as convective stirring using a stirring bar to stir the solution, or in the form of ultrasonic energy in which the solution is sonicated. For example, a combination of convective stifling and sonication can be used, where sonication is employed in an initial stage and stifling is employed in later stages. The dispersion is an oxidized carbon nanotube-chemical oxidant in the acid solution.

For example, the dispersion can be first sonicated without heat for 1 to 24 hours, subsequently, the dispersion can be stirred and heated to 45 to 70° C. for another 1 to 24 hours, and the dispersion can be stirred and cooled to 20 to 40° C. for 1 to 5 days.

The process further includes filtering the dispersion with deionized water until the pH of the filtrate is 7 or neutral.

The resulting of the filtering is heated to 70 to 120° C. for 1 to 24 hours by oven drying to create a carbon nanotube powder.

The process further comprises placing the carbon nanotube powder in deionized water and depositing the same as a thin film by filtration onto a surface which may be removed or dissolved.

The process further comprises placing or depositing the resulting CNT thin film on a surface such as alumina (aluminum oxide), silica (silicon dioxide), or other insulating dielectric surface This surface has an electrical contact. The electrical contact is a conductive material or polymer, for example, a silver epoxy, or by which electrical contact is made by depositing the CNT thin film onto an insulating dielectric surface where an interdigital conductive pattern of gold, silver, platinum, or other conductive metal has been pre-deposited for making contact to the CNT thin film.

The CNT condensation sensor made by the above process is configured to be sensitive to polar molecules such as water ($H_2O$) or ammonia ($NH_3$), very insensitive to non-polar molecules such as oxygen ($O_2$), nitrogen ($N_2$), hydrogen ($H_2$), carbon dioxide ($CO_2$), and hydrocarbon molecules such as methane ($CH_4$), ethane ($C_2H_6$), propane ($C_3H_8$), and butane ($C_4H_{10}$). Furthermore, the CNT condensation sensor is extremely sensitive to polar liquid water and extremely insensitive to nonpolar solid water (ice). Consequently, the CNT condensation sensor can detect the formation of liquid phase water; can detect the formation of solid phase water (ice); and can distinguish between liquid water condensation and solid water (ice condensation).

Also disclosed is a method for measuring dew point with a CNT condensation sensor. The method includes controlling a temperature of a surface. The CNT condensation sensor is mounted to the surface. The temperature is initially started a high surface temperature, e.g., a maximum temperature $T_{high}$. $T_{high}$ is above 0° C. in order to melt any ice and evaporate water on the CNT condensation sensor surface and below 100° C. to prevent boiling or extreme conditions that would destroy the surface of the CNT condensation sensor. For example, $T_{high}$ may be a temperature between 30° C. and 70° C. In an aspect of the disclosure, if measuring dew points below 20° C., $T_{high}$ is between about 30° C. and 40° C.

The temperature is controlled by decreasing the temperature of the surface $T_{surface}$ on which the CNT condensation sensor is mounted at a controllable scan rate $dT_{surface}/dt$ with time t. The controllable scan rate is variable. In an aspect of the disclosure, the scan rate is held constant over any temperature range in which a dew point determination is being made by mathematical calculation and analysis.

The scan rate $dT_{surface}/dt$ may be between 0.001° C./sec to 10° C./sec. A Fast scan is defined between about 0.1 and about 10° C./sec and provides a quick measurement determination but with low precision. Alternatively, a slow scan rates is defined as between about 0.001 and about 0.1° C./sec providing well defined sharp curves of high precision. However, a slow scan may take very long measurement times.

In an aspect of the disclosure, multiple scans can be used. For example, initially a fast scan can be used to approximate the region of the dew point and a second slower scan, which can be implemented in a narrower range in the vicinity of the appropriated dew point can be used.

The method may also include determining the scan rate for controlling the decrease of the temperature.

The method further includes simultaneously measuring or detecting the resistance of the CNT condensation sensor while controlling the temperature of the temperature controlled surface.

The method may also include determining an ice point $T_{ice}$. The ice point $T_{ice}$ is a temperature which is determined by the peak in CNT condensation sensor resistance $R_{cnt}$ versus the surface temperature $T_{surface}$. $T_{ice}$ is where condensed water is freezing and forming water or ice. $T_{ice}$ is indicated by and corresponds to the surface temperature $T_{surface}$ at which 1) the slope is negative for temperatures above $T_{ice}$, that is the $1^{st}$ derivative $dR_{cnt}/dT_{surface} < 0$ for $T > T_{ice}$; 2) the slope is positive below $T_{ice}$, that is $dR_{cnt}/dT_{surface} > 0$ for $T < T_{ice}$, 3) the change in slope is zero or undefined at the ice point $T_{ice}$, that is the $2^{nd}$ derivative $d^2R_{cnt}/dT^2_{surface} = 0$ at $T_{ice}$ or is undefined, 4) conditions 1-3 resulting in a maximum extremum or "peak" in the $R_{cnt}$ (ohms) versus $T_{surface}$ (° C.) curve where $T_{surface}$ (° C.) equals $T_{ice}$(° C.), and 5) immediately following $T_{ice}$ (° C.), as the surface temperature is further decreased during the scan, the magnitude of the CNT resistance $R_{CNT}$ (ohms) drops off abruptly in magnitude providing the characteristic icing signature.

The temperature is decreased at the chosen scan rate until the ice point $T_{ice}$ is reached. The ice point $T_{ice}$ is lower than the dew point $T_{dew}$. Therefore, at the ice point $T_{ice}$, the scan has passed the dew point $T_{dew}$, deposited moisture, and created ice on the surface.

The method includes determining the dew point.

For dew point temperatures $T_{dew}$ above 0 (° C.) and a temperature scanning rates of approximately 0.1° C./sec or slower, the dew point $T_{dew}$ is the surface temperature $T_{surface}$ which corresponds to an inflection temperature $T_{inflection}$. The inflection temperature is determined as follows: 1) the slope or $1^{st}$ derivative $dR_{cnt}/dT_{surface}$ is a minimum; 2) the slope is negative or $1^{st}$ derivative $dR_{cnt}/dT_{surface} < 0$ for both $T > T_{inflection}$ and $T < T_{inflection}$; and 3) the change in slope is zero at $T_{inflection}$ or $2^{nd}$ derivative $d^2R_{cnt}/dT^2_{surface} = 0$, and 4) the "change in slope" or "$2^{nd}$ derivative $d^2R_{cnt}/dT^2_{surface}$" (ohms/° C./° C.) is positive (or >0) for surface temperatures $T_{surface}$ (° C.) above $T_{inflection}$ (° C.) and negative (or <0) for surface temperatures $T_{surface}$ (° C.) below $T_{inflection}$ (° C.). For dew point temperatures $T_{dew}$ above 0 (° C.) and temperature scanning rates of ~0.1° C./sec or slower, the ice point $T_{ice}$ will be close to 0° C.

For dew point temperatures $T_{dew}$ above 0 (° C.) and for faster scan rates above $dT_{surface}/dt$ approximately 0.1° C./sec where fluid momentum, energy (thermal), and mass (diffusion) transfer limitations, in addition to adsorption and condensation kinetic limitations become important, the CNT resistance $R_{CNT}$ (ohms) versus surface temperature $T_{surface}$ (° C.) is shifted lower and becomes broader, the temperature inflection point $T_{inflection}$ (° C.) determines the dew point $T_{dew}$ (° C.) via empirical correlation for a fixed set of parameters such as flow rate, gas temperature and pressure, cell design, and temperature scan rate.

For dew point temperatures $T_{dew}$ below 0 (° C.) and temperature scanning rates of ~0.1° C./sec or slower, the ice point $T_{ice}$ (° C.) as described above is the "frost point" $T_{frost}$ (° C.) from which the dew point $T_{dew}$ (° C.) may be calculated.

For dew point temperatures $T_{dew}$ below 0 (° C.) and for faster scan rates above $dT_{surface}/dt$ approximately 0.1° C./sec, broader curves result where the ice point $T_{ice}$ and the inflection point $T_{inflection}$ become further apart where fluid momentum, energy (thermal), and mass (diffusion) transfer limitations, in addition to adsorption and condensation kinetic limitations become important, the ice point $T_{ice}$ (° C.) and/or the inflection point $T_{inflection}$ (° C.) which becomes discernable for fast scan rates allows the determination of the frost point $T_{frost}$ (° C.) and the dew point $T_{dew}$ (° C.) via empirical correlation for a fixed set of parameters such as flow rate, gas temperature and pressure, cell design, and temperature scan rate.

After a scan, the surface temperature $T_{surface}$ is scanned or returned to the initial high temperature $T_{high}$ by heating the surface, melting ice on the CNT condensation sensor, evaporating water from the CNT condensation sensor, drying the CNT condensation sensor, and preparing for a subsequent scan.

For subsequent scanning, a control of the temperature using a fast scan rate of the temperature $dT_{surface}/dt$ may be utilized to bring the surface temperature near that of a previous fast scan, then switching to a slow scan $dT_{surface}/dt$ in order to obtain a dew point $T_{dew}$ determination of higher precision. Below 0° C., a very slow scans $dT_{surface}/dt$ of around 0.001 to 0.01° C./sec result in the inflection point and the ice point converging, giving a high degree of certainty in the frost point determination, from which the dew point can be calculated from.

In an aspect of the disclosure, the temperature can be scanned from +70 down to ~120° C. and dew points $T_{dew}$ can be determined in a range from ~110° C. up to +60° C.

Also disclosed is a chemically activated carbon nanotube (CNT) sensor:
which is sensitive to polar molecules and insensitive to nonpolar molecules;
which is able to measure the dew point of polar molecules in a gas mixture where the other constituents are nonpolar molecules;
which is able to measure the dew point of a target polar molecule in a background gas stream consisting of nonpolar molecules and polar molecules in which the dew point of the background polar molecules is lower than the dew point of the target polar molecules;
which is specifically sensitive to the polar molecule water ($H_2O$);
which is specifically sensitive to the polar molecule ammonia ($NH_3$);
which is sensitive to polar molecules in addition to water ($H_2O$) or ammonia ($NH_3$) including the following chemical groups: alkyl halides, alcohols, aldehydes, ketones, carboxylic acids, amines, esters, and any other polar molecule as determined by its dipole moment in which polar molecules will typically be considered as having a dipole moment of ~0.5 to 3 debye: water (1.85 debye) and ammonia (1.47 debye) for example;
which is very insensitive to non-polar molecules such as oxygen ($O_2$), nitrogen ($N_2$), hydrogen ($H_2$), carbon dioxide ($CO_2$), and hydrocarbon molecules such as methane ($CH_4$), ethane ($C_2H_6$), propane ($C_3H_8$), and butane ($C_4H_{10}$) as determined by its dipole moment in which non-polar molecules will typically be considered as having a dipole moment of approximately 0 to 0.2 debye;
which has a sensitivity that is greatest for polar molecules having large dipole moments greater than about 1.4 debye—water (1.85 debye) and ammonia (1.47 debye) for example—measured in gas streams containing non-polar molecules having dipole moments close to zero—air (0 debye), nitrogen (0 debye), oxygen (O debye), carbon dioxide (0 debye), hydrogen (0 debye), methane (0 debye), ethane (0 debye), ethylene (0 debye), propane (0.08 debye), carbon monoxide (0.11 debye), benzene (0 debye), and others in which the dipole moment is small, typically less than approximately 0.1 debye;
which detects the dew point of water ($H_2O$) in non-polar inorganic gas streams such as oxygen, nitrogen, air, hydrogen, helium, argon, sulfur hexafluoride, and silane;
which detects the dew point of water in carbon dioxide, a gas which reacts with water to form carbonic acid;
which detects the dew point of water in hydrocarbon streams such as methane, ethane, ethylene, propane, butane, pentane, hexane, heptane, octane, benzene, and other hydrocarbons with small dipole moments;
which may be heated to clean condensate—liquid or solid—of the surface of the CNT prior to a measurement;
which allows the measurement of dew point by a inflection where a slope change is detected and baseline resistance is not important; and
which determines an ice point indicated by a peak in resistance which confirms a dew point indicated by a slope change at a slightly higher temperature.

Aspect of the disclosure can be used to determine the dew points of non-polar gases. For example, for non-polar gases which do not react with water and have pure gas component dew points less than the lowest water dew point of interest, typically −110° C., such as air, oxygen, nitrogen, and hydrogen. The dew point can be determined using aspects of the disclosure where the temperature of the surface on which a CNT condensation sensor and a temperature sensor are mounted is decreased until an icing point is reached and a dew point, which is just slightly above the icing point, is determined by a temperature at which an absolute value of the slope of CNT resistance with respect to surface temperature (dR/dT) is minimized and the change in slope or second derivative ($d^2R/dT^2$) is zero, e.g., the inflection point. Below 0° C., with very slow scan rates, the icing (frost) point which is a peak converges with the inflection point making it very precise to determine.

Additionally, for example, carbon dioxide is a non-polar gas, which is reactive with water to form carbonic acid, has a triple point @ 5.11 atm of −56.6° C., and a sublimation point @ 1 atm of −78.5° C. As a non-polar gas, the CNT condensation will not be sensitive to it; however, below the triple point listed above, condensation can occur that would block the surface to water diffusion and adsorption and below the sublimation point solid carbon dioxide depositing and covering the surface can occur. An operation at 1 atm, allows for an operation down to −78.5° C. before consideration of its presence is needed. For lower dew points, a fast scan can be used in the dew point determination.

Further, for example, for non-polar hydrocarbon gases such as methane (−162° C.), ethane (−88.5° C.), propane (−42° C.), and n-butane (0° C.), where the value in parenthesis is the boiling point or the pure component dew point. Methane and ethane will typically not pose a problem since their pure component dew points are typically below the moisture levels of interest; however, hydrocarbons propane and n-butane have pure component dew points in the range of typical application interest. The CNT condensation sensor is chemically activated to sense polar molecules, so no interference due to hydrocarbon condensation is expected; however, hydrocarbon condensation can block the surface hindering diffusion and adsorption of water. In this case, a fast scanning can be used to minimize the effects of hydrocarbon condensation, and a shift in baseline can be ignored since an inflection point is measured, e.g., slope and changes in slope to make a determination in water dew point along with confirmation by the icing peak.

Aspect of the disclosure can be used to determine the dew points of polar gases. For example, ammonia is polar gas, which is reactive with water to form a weak basic solution of ammonium hydroxide, and pure ammonia has a dew point of about −33.3° C. Determining water dew point above this is done as before. In fact, the dew point of ammonia or ammonia at a lower concentration in a gas matrix could also be determined by the sensor by fast scanning of temperature to prevent the onset of icing. At low water concentration, an estimate of the dew point can be done by fast scanning of the temperature because the baseline shifts can be ignored, as long as the inflections indicated by slope and changes in slopes due to phase inflections occurring can be determined. If there is sufficient difference in the ammonia dew point and the water dew point, then the inflections can be determined.

DETAILED DESCRIPTION

In an aspect of the disclosure, the system 1 includes a Processor 35. The Processor 35 can be a CPU. The CPU is configured to execute one or more programs stored in a computer readable storage device. The computer readable storage device can be RAM, persistent storage or removable storage. For example, the CPU can execute instructions in a program that may be loaded into RAM.

Computer readable storage device (not shown) may be in a tangible or hardware form, such as, an optical or magnetic disc that is inserted or placed into a drive or other portion or device for transfer onto an internal storage device, such as a hard drive. Additionally, the computer readable storage device also may take the form of a hard drive, a thumb drive, or a flash memory that is connected to CPU.

The Processor 35 may include one or more processing units.

RAM, ROM and Persistent Storage are only examples of Data Storage Devices. A storage device is any piece of hardware that is capable of storing information, such as, for example without limitation, data, programs, instructions, program code, and/or other suitable information either on a temporary basis and/or a permanent basis.

Persistent Storage can take various forms. For example, Persistent Storage can contain one or more components or devices. For example, Persistent Storage may be a hard drive (e.g., HDD), a flash memory, a rewritable optical disk, a rewritable magnetic tape, or some combination of the above. The medium or media used by Persistent Storage also may be removable. For example, a removable hard drive may be used.

Alternative, the Processor 35 can be a FPGA or PAL.

The system 1 includes an input device (not shown) for inputting parameter used by the system such as, but not limited to, the $T_{high}$, $T_{low}$ and scan rate.

Figure 1:
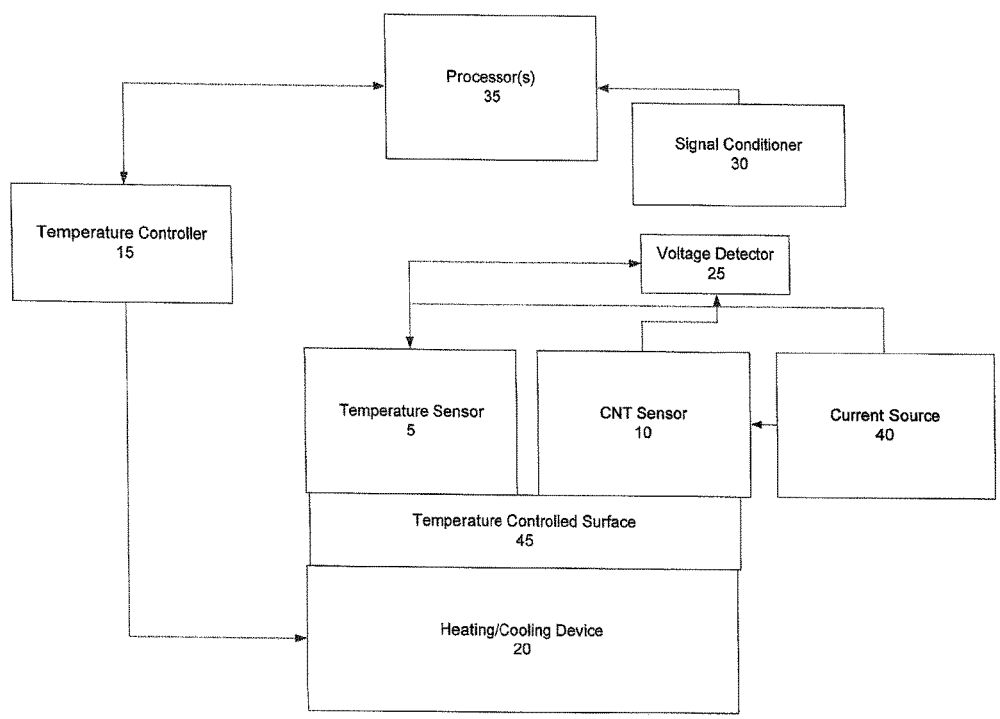
FIG. 1 illustrates a block diagram of a system for detecting a dew point in accordance to aspects of the disclosure.

The system 1 also includes a Temperature Controller 15 configured to control the scanning of the temperature of a Temperature Controlled Surface 35 according to the scan rate. FIG. 1 depicts one Temperature Controller 15; however, more than one Temperature Controller 15 can be used. For example, one Temperature Controller 15 can be used to scan the temperature from a $T_{high}$ to a $T_{low}$ and a second Temperature Controller 15 can be used to scan the temperature from a $T_{low}$ to $T_{high}$.

The Temperature Controller 15 controls a Heating/Cooling Device 20 to heat or cool the Temperature Controller Surface 45. Heating/Cooling Device 20 may be a thermoelectric peltier device such as a multi-stage thermoelectric device. Alternatively, the Heating/Cooling Device 20 can be a cryogenic cooling "finger" with at least one heating coil. Other Heating/Cooling Device 20 such as, but not limited to, a refrigerant cooled thermoelectric peltier or a cryogenic cooled thermoelectric peltier device may also be used.

The system 1 also includes a Temperature Sensor 5 and carbon nanotube (CNT) sensor 10 (also described as a carbon nanotube (CNT) condensation sensor). The Temperature Sensor 5 used to measure temperature in the vicinity of the Temperature Controller Surface 45 simultaneously and the CNT sensor detection of humidity. The Temperature Sensor 5 can be a platinum resistance temperature detector (RTD) to precisely measure the temperature of the temperature controlled surface. For example, a 100Ω platinum RTD can be used. The Temperature Sensor 5 may or may not be mounted to the Temperature Controlled Surface 45.

The CNT Sensor 10 is mounted to the Temperature Controlled Surface 45. The Temperature Controlled Surface 45 can be a copper metal sheet.

Both the CNT Sensor 10 and the Temperature Sensor 5 are electrically coupled to a constant Current Source 40. The Current Source 40 supplies a current to the sensors. For example a DC current of 10 µA can be supplied to the sensors.

During the controlled temperature scan, a Voltage Detector 25 detects the voltage thru or across the sensors, e.g., Temperature Sensor 5 and CNT Sensor 10. Since a constant current is supplied to the sensors, the detected voltage is proportional to the resistance, e.g., change is resistance of the sensors. The change in resistance of the CNT Sensor 10 is due to a humidity change. The change in resistance of the Temperature Sensor 5 is due to a change in temperature.

The Voltage Detector 25 is in electrical communication with the Temperature Sensor 5 and CNT Sensor 10 to enable the Voltage Detector to monitor the change of voltage, e.g., via two different input connections: one for each sensor output, respectively.

The Voltage Detector 25 is in electrical communication with a Signal Conditioner 30, similarly with two different connections one for each sensor output, respectively. The resistance of the CNT Sensor 10, the resistance of the Temperature Sensor 5 is stored is a storage device for use by the Processor 35.

As the temperature of the Temperature Controlled Surface 45 is controlled by the Temperature Controller 15 via the temperature sensor, the change in the measured voltages from the Temperature Sensor 5 and CNT Sensor 10 are continuously recorded and stored.

For each new voltage values, the Processor 35 retrieves the stored values and calculates the resistance value and determines the change in resistance value divided by the change in temperature value as a function of temperature, e.g., first derivative as a function of temperature. The Processor 35 also calculates the change in the slope of the resistance divided by the change in temperature value verses temperature, e.g., second derivative as a function of temperature. These calculations are used by the Processor 35 to determine the ice point $T_{ice}$, frost point $T_{frost}$, and dew point $T_{dew}$, among other features.

The constant current value supplied by the Current Source 40 is also stored in the storage device such that the Processor 35 can calculate the resistance values from the measured voltages.

Figure 2:
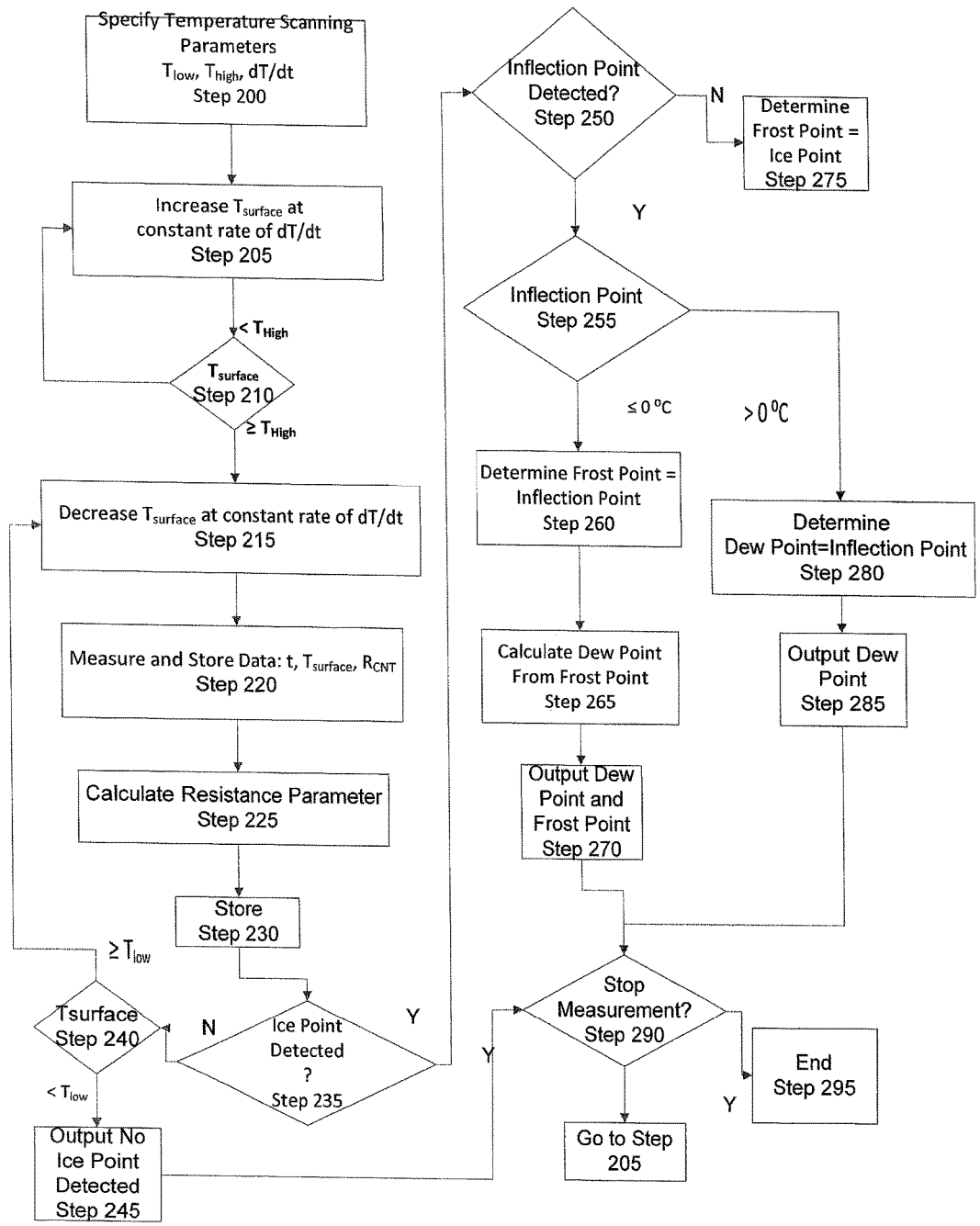
FIG. 2 illustrates a flow chart of a method for detecting a dew point in accordance to aspects of the disclosure.

FIG. 2 illustrates a method of determining a dew point and/or frost point of a sample under testing. At Step 200, the configuration parameters are input. For example, the scanning rate can be set. The scan rate $dT_{surface}/dt$ may be between 0.001° C./sec to 10° C./sec. A Fast scan is defined between about 0.1 and about 10° C./sec and provides a quick measurement determination but with low precision. Alternatively, a slow scan rates is defined as between about 0.001 and about 0.1° C./sec providing well defined sharp curves of high precision. Alternatively, a fast scan can be between 1 and about 10° C./sec. A slow scan rate can be between about 0.001 and about 0.1° C./sec and an intermediate scan rate can be used between about 0.1 and about 1° C./sec.

If multiple scans are conducted, a first scan can use a fast scan rate while the second or subsequent scan can use a slower rate over a narrower temperature range.

Additionally, at Step 200, the scanning range is set, e.g., $T_{high}$ and $T_{low}$. $T_{high}$ is above 0° C. in order to melt any ice and evaporate water on the CNT condensation sensor surface and below 100° C. to prevent boiling or extreme conditions that would destroy the surface of the CNT condensation sensor. In an aspect of the disclosure, $T_{high}$ may be a temperature between 30° C. and 70° C. In another aspect of the disclosure, if measuring dew points below 20° C., $T_{high}$ is between about 30° C. and 40° C.

The parameters are stored. The stored parameters are made available to the Temperature Controller 15. In another aspect of the disclosure, the configuration parameters are directly input into the Temperature Controller 15.

At Step 205, the Temperature Controller 15 controls the Heating/Cooling Device 20 to increase the surface temperature of the Temperature Controlled Surface 45. This is to ensure that the surface temperature $T_{surface}$ starts at $T_{high}$. For subsequent scans this also assures that the surface of the CNT Sensor 10 is back to a baseline.

The change in temperature is detected by the Temperature Sensor 5 in the form of a voltage change measured by the Voltage Detector 25 which is output to the Signal Conditioner and Processor 35. The Processor 35 determines the surface temperature $T_{surface}$ at Step 210 based on the change in resistance. If the surface temperature is not greater than or equal to $T_{high}$, the Processor 35 notifies the Temperature Controller 15 to continue increasing the temperature of the surface of the Temperature Controlled Surface 45, e.g., returns to Step 205. Otherwise, the Processor notifies the Temperature Controller 15 to stop increasing the temperature. At Step 215, the Temperature Controller 15 starts to decrease the temperature of the Temperature Controlled Surface 45 in accordance with the set scan rate. FIG. 2 notes that the scan rate is constant; however, in accordance with another aspect of the disclosure, the scan rate can be variable, e.g., fast scan rates at high temperatures and slower scan rates at lower temperatures.

While the Temperature Controller 15 controls the temperature of the Temperature Controlled Surface 45 to the set scan rate, the voltages, e.g., voltage change from both Sensors (Temperature Sensor 5 and CNT Sensor 10 are detect by the Voltage Detector 25 (Step 220). The Signal Conditioner 30 receives the detected voltages and relays the same to the Processor 35.

At Step 220, the Processor 220 calculates the surface temperature ($T_{surface}$) and the resistance of the CNT Sensor ($R_{CNT}$) using the received and storage voltages and the known constant current. The scan time is also simultaneously recorded and stored.

At Step 225, the Processor 225 calculates at least one resistance parameter such as the first and second derivative of resistance verses temperature. The first and second derivatives are based on the currently determined resistance and temperature values and previously determined and stored resistance and temperature values, respectively.

The resistance parameters are stored in Step 230.

At Step 235, the Processor determines if an Ice Point $T_{ice}$ is detected.

Figure 3:
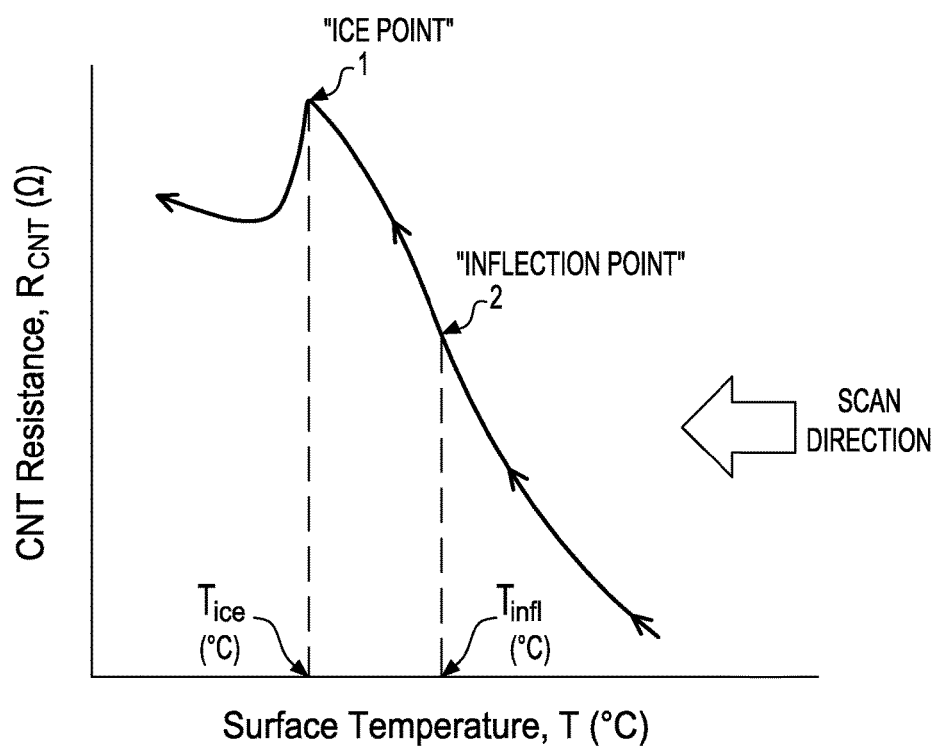
FIG. 3 illustrates an example of a surface temperature and resistance of the CNT condensation sensor chart as a result of a temperature scanning in accordance to aspects of the disclosure.

FIG. 3 illustrates an example of a CNT Resistance and temperature chart. As noted in FIG. 3, the scan direction is from $T_{high}$ to $T_{low}$. The ice point on the chart is identified by a circle and labeled 1. "Ice Point". A vertical dash line from the curve down to the Surface temperature axis identifies the temperature $T_{ice}$. The Surface Temperature is in degrees C. The CNT resistance is in ohms. The resistance is on the Y-axis and the temperature is on the X-axis.

Figure 4:
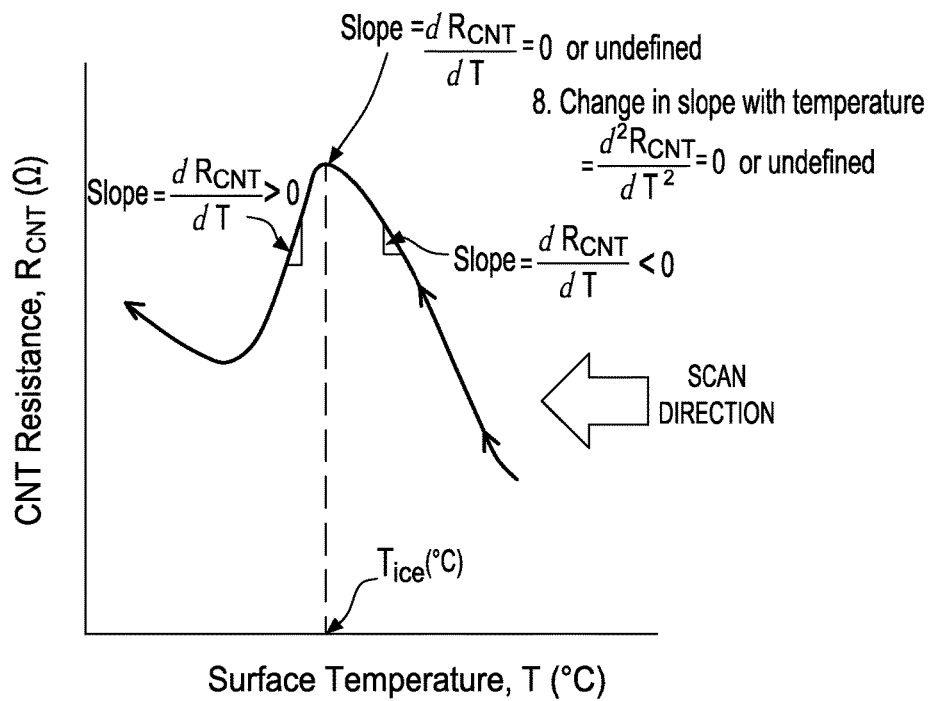
FIG. 4 illustrates an example determination of an ice point using a surface temperature and CNT resistance chart in accordance with aspects of the disclosure.
Figure 5:
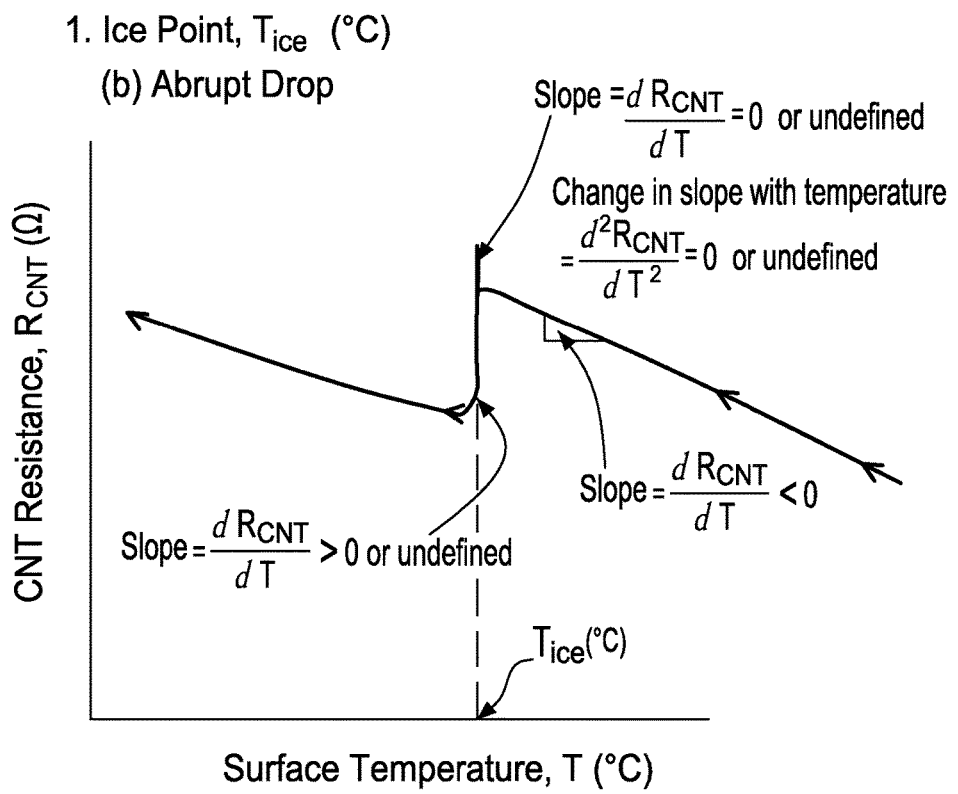
FIG. 5 illustrates a second example determination of an ice point using a surface temperature and CNT resistance chart in accordance with aspects of the disclosure.
Figure 6:
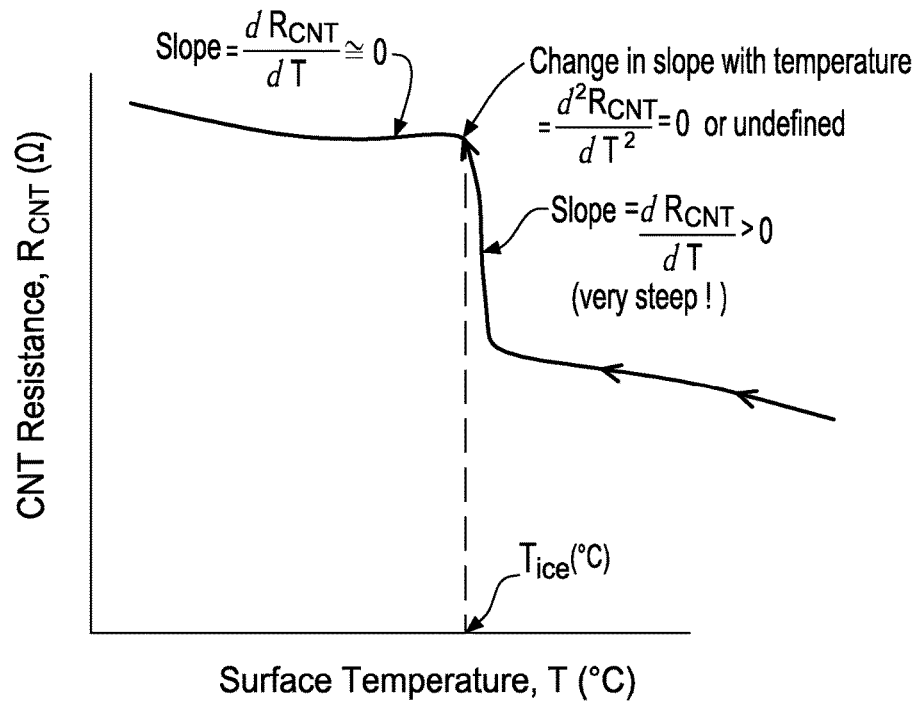
FIG. 6 illustrates a third example determination of an ice point using a surface temperature and CNT resistance chart in accordance with aspects of the disclosure.

FIGS. 4-6 illustrate various ways to determine the ice point in accordance with aspects of the disclosure.

An ice point can be indicated by a) peak of, (b) an Abrupt Drop or a (c) Plateau. FIG. 4 illustrates determining the ice point based on the peak; FIG. 5 illustrates determining the ice point based on an abrupt drop; and FIG. 6 illustrates determining the ice point based on a plateau.

As with FIG. 3, FIG. 4 also illustrates an example of a chart showing a relationship between resistance $R_{CNT}$ of the CNT sensor 10 and the surface temperature $T_{surface}$ over the temperature scan.

A peak can be identified when:
1. The Slope at the point is zero or undefined (at the $T_{ice}$), e.g., $dR_{cnt}/dT_{surface}$=zero or undefined;
2. The change in the slope with temperature $d^2R_{cnt}/dT_{surface}2$ is zero or undefined (at the $T_{ice}$);
3. The Slope is less than zero for temperatures greater than $T_{ice}$, e.g., $dR_{CNT}/dT_{surface}$<0; and
4. The Slope is greater than zero for temperatures less than $T_{ice}$ and near $T_{ice}$, e.g., $dR_{CNT}/dT_{surface}$>0.

As shown in FIG. 4, at some temperature below $T_{ice}$, the slope returns to a negative value.

FIG. 4 identifies the Slope at the ice point is zero or undefined by a circle along with the change in the slope with temperature $d^2R_{cnt}/dT_{surface}2$ at the ice point. A vertical dash line from the curve down to the Surface temperature axis identifies the temperature $T_{ice}$.

On the right side of $T_{ice}$ in the figure, a negative slope is shown and identified by an arrow and on the left side of $T_{ice}$ in the figure, a positive slope is shown and also identified by an arrow.

FIG. 5 also illustrates an example of a chart showing a relationship between resistance $R_{CNT}$ of the CNT sensor 10 and the surface temperature $T_{surface}$ over the temperature scan (different chart from FIGS. 3 and 4).

An abrupt change is identified when:
1. The Slope at the point is zero or undefined (at the $T_{ice}$), e.g., $dR_{cnt}/dT_{surface}$=zero or undefined;
2. The change in the slope with temperature $d^2R_{cnt}/dT_{surface}^2$ is zero or undefined;
3. The Slope is less than zero for temperatures greater than $T_{ice}$, e.g., $dR_{CNT}/dT_{surface}$<0; and
4. The Slope is greater than zero for temperatures less than $T_{ice}$, and near $T_{ice}$, e.g., $dR_{CNT}/dT_{surface}$>0.

As shown in FIG. 5, at some temperature below $T_{ice}$ and near $T_{ice}$, the slope returns to a negative value.

FIG. 5 identifies the Slope at the ice point is zero or undefined by a circle alone with the change in the slope with temperature $d^2R_{cnt}/dT_{surface}2$. A vertical dash line from the curve down to the Surface temperature axis identifies the temperature $T_{ice}$.

On the right side of $T_{ice}$ in the figure, a negative slope is shown and identified by an arrow and on the left side of $T_{ice}$ in the figure, a positive slope is shown and also identified by an arrow with a circle.

FIG. 6 also illustrates an example of a chart showing a relationship between resistance $R_{CNT}$ of the CNT sensor 10 and the surface temperature $T_{surface}$ over the temperature scan (different chart from FIGS. 3-5).

A plateau is identified when:
1. A change in the slope with the temperature is approximate 0, e.g., $d^2R_{cnt}/dT_{surface}2$ approximately zero at $T_{ice}$;
2. The slope $dR_{CNT}/dT_{surface}$<0 and is very steep for temperatures greater than $T_{ice}$; and
3. The slope $dR_{CNT}/dT_{surface}$ is approximate zero for temperatures less than $T_{ice}$.

FIG. 6 identifies the change in the slope at the ice point being zero by an arrow. On the left hand side of the figure, e.g., temperatures less than the $T_{ice}$ a circle identifies where the slope is approximately zero and on the right side of the figure, e.g., temperatures greater than the $T_{ice}$ the slope is steep, is less than zero and is identified by an arrow. A vertical dash line from the curve down to the Surface temperature axis identifies the temperature $T_{ice}$.

The scan rate may impact which way the ice point is determined. For example, at slow temperature scan rates, a well defined peak may be observed as illustrated in FIG. 4. As the scan rate increases, the peak may change into an abrupt drop as illustrated in FIG. 5.

Additionally, the temperature at which the frost/dew point is may also affect the way the ice point is determined. For example, for scans where the frost point or dew point is very low or where there is a gas having very low moisture content, a plateau relationship may be observed as illustrated in FIG. 6.

At Step 235, if an Ice Point $T_{ice}$ is not detected, the surface temperature of the Temperature Controller Surface 45 is determined (step 240). If surface Temperature is equal to or less than the low temperature for the scan, the Processor 35 outputs a "No Ice Point" detection result at Step 245. Otherwise, the Processor 35 notifies the Temperature Controller 15 to continue to decrease the surface temperature at the set rate.

If an ice point $T_{ice}$ is detected at Step 235, the Processor 35 determines if an inflection point occurred at Step 250.

Figure 7A:
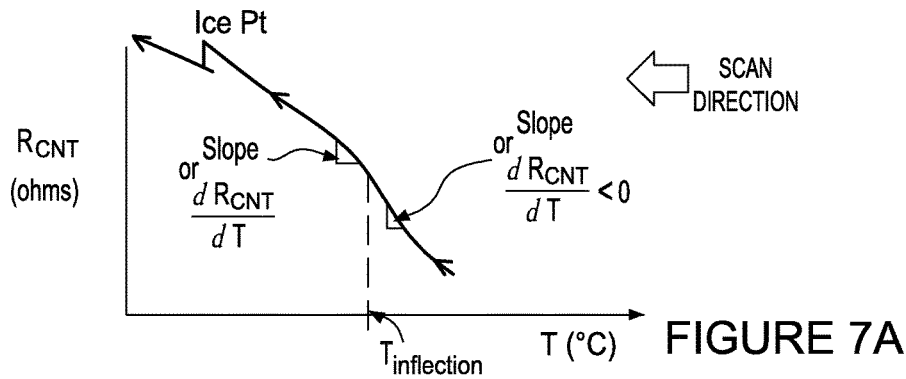
FIGS. 7A-7C illustrate examples of CNT sensor resistance and temperature relationships in accordance with aspects of the disclosure.
Figure 7B:
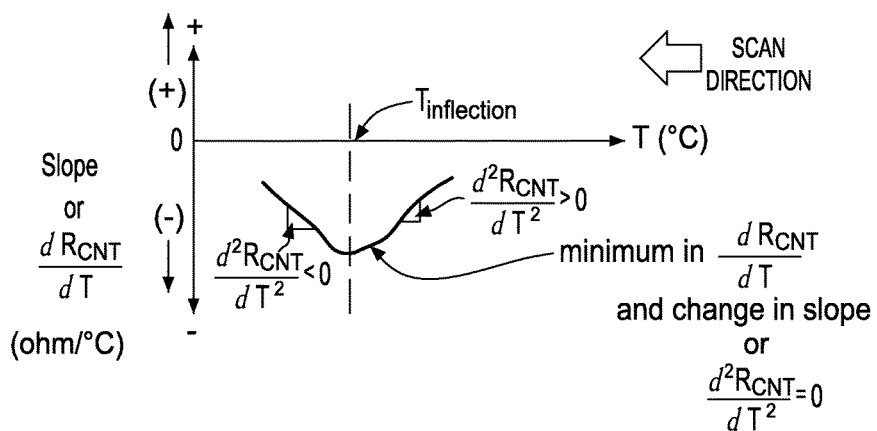
Figure 7C:
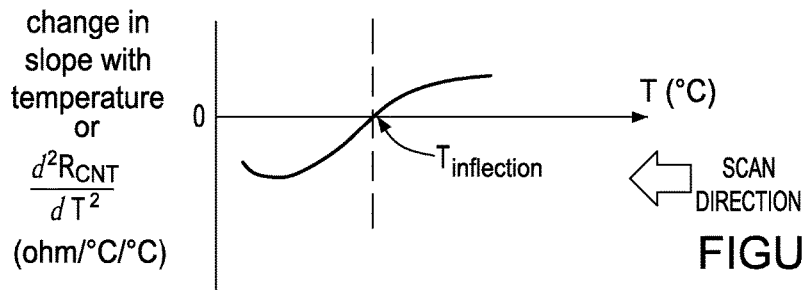

FIGS. 7A-7C illustrate examples of CNT sensor resistance and temperature relationships. FIG. 7A depicts a relationship between CNT sensor resistance as a function of temperature. FIG. 7B depicts a relationship between a first derivative resistance divided by temperature and a function of temperature. FIG. 7C depicts a relationship between a second derivative of resistance as a function of time. Each of these figures shows a criteria for detecting an inflection point.

An inflection point is identified by:
1. The slope $dR_{CNT}/dT_{surface}$<0 for Temperature greater than or equal to $T_{inflection}$ and The slope $dR_{CNT}/dT_{surface}$<0 for Temperature greater than or equal to $T_{inflection}$ (FIG. 7A);
2. $d^2R_{cnt}/dT_{surface}^2$ is zero at $T_{inflection}$ (FIG. 7B); and
3. $d^2R_{cnt}/dT_{surface}^2$ is greater than zero for temperatures greater than $T_{inflection}$ and $d^2R_{cnt}/dT_{surface}^2$ is less than zero for temperatures less than $T_{inflection}$ (FIG. 7C).

If an inflection point is detected at Step 250, the Processor identifies the temperature of the inflection point at Step 255. If the identified inflection temperature $T_{inflection}$, is less than or equal to zero, then the Processor 35 sets the inflection temperature to the frost point ($T_{frost}$) at step 260. The $T_{inflection}$ and $T_{frost}$ are stored.

At Step 265, the Processor 35 calculates the dew point $T_{dew}$ from the $T_{frost}$. Above, 0° C., water vapor in a gas phase condenses as liquid water on a solid surface. Thus, results in a dew point. However, at or below 0° C., water vapor in the gas phase typically condenses as ice (frost) on a solid surface—a frost point; however, under special conditions water vapor in the gas phase may condense as supercooled water on a solid surface—a dew point. But, supercooled is not stable; it is metastable and will eventually convert into ice (frost) at temperatures at or below 0° C. The CNT sensor is able to distinguish between liquid water (polar) and ice (frost) (nonpolar).

In an aspect of the disclosure, the dew point $T_{dew}$ can be calculated from the $T_{frost}$ using the Goff Gratch equations and either a look up table or polynomial equation derived from the Goff Gratch equations.

$$\text{Log}_{10} e_i = -9.09718(273.16/T - 1) - 3.56654 \text{ Log}_{10}(273.16/T) + \quad [1]$$
$$0.876793 (1 - T/273.16) + \text{Log}_{10}(6.1071)$$

with T in [K] and $e_i$ in [hPa].

The equation outputs the vapor pressure over ice. Water concentration in the vapor phase in equilibrium over the ice (frost) is $e_i$ in hPa or mb. Equation 1 provides a means to calculate the water vapor pressure over ice (frost) for a given temperature and applies for temperatures between from 0° C. down to −110° C.

$$\text{Log}_{10} e_w = -7.90298 (373.16/T - 1) + \quad [2]$$
$$5.02808 \text{ Log}_{10}(373.16/T) - 1.3816 \ 10^{-7}(10^{11.344(1-T/373.16)} - 1) +$$
$$8.1328 \ 10^{-3}(10^{-3.49149(373.16/T-1)} - 1) + \text{Log}_{10}(1013.246)$$

with T in [K] and $e_w$ in [hPa]

The equation outputs the vapor pressure over liquid water. The temperature is absolute temperature (K): K=° C.+273.15 where ° C.=(° F.−32)/1.8 or ° F.=1.8×° C.+32. Water concentration in the vapor phase is $e_w$ in hPa or mb. Equation 2 provides a means to calculate the water vapor pressure over liquid water for a given temperature and applies for temperatures between 0° C. and 100° C. For temperatures below 0° C., Equation 2 can be used to extrapolated and used to calculate the water vapor pressure over supercooled water.

Specifically, Equation 2 is used to generate a look up table of vapor pressure and temperature. For example, x sample points can be used to generate a table of vapor pressure verses temperature. In an aspect of the disclosure at least 10 sample points can be used. In another aspect of the disclosure at least 50 sample points can be used. The look up table can be subsequently used to extrapolate a temperature based on a vapor pressure determined from equation 1 using the vapor pressure determined from equation 1 as a look up key. Alternatively, instead of using a look up table, a polynomial equation can be generated which characterizes the relationship between vapor pressure and temperature.

The total pressure in a gas phase is the sum of the components and for air: $P_{total} = P_{oxygen} + P_{nitrogen} + P_{water\ vapor} + \ldots$ other trace gases.

Afterwards, the Processor 35 outputs both the dew point $T_{dew}$ and $T_{frost}$ at Step 270.

If, at Step 250, no inflection point was detected, the Processor 35 set the ice point, $T_{ice}$ as the frost point $T_{frost}$.

If, at Step 250, inflection point $T_{inflection}$ was detected, and the identified temperature of the inflection point is greater than zero, the Processor 35 set the inflection point, $T_{inflection}$ as the dew point $T_{dew}$.

The Processor 35 then outputs the determined dew point $T_{dew}$ at Step 285.

After Steps 245, 270 and 285, the Processor 35 determines if the measurement should be stopped or another scan performed. If yes, the process ends at step 295. Otherwise, the process returns to Step 205 for increasing the temperature of the surface of the Temperature Controlled Surface 45.

Figure 8:
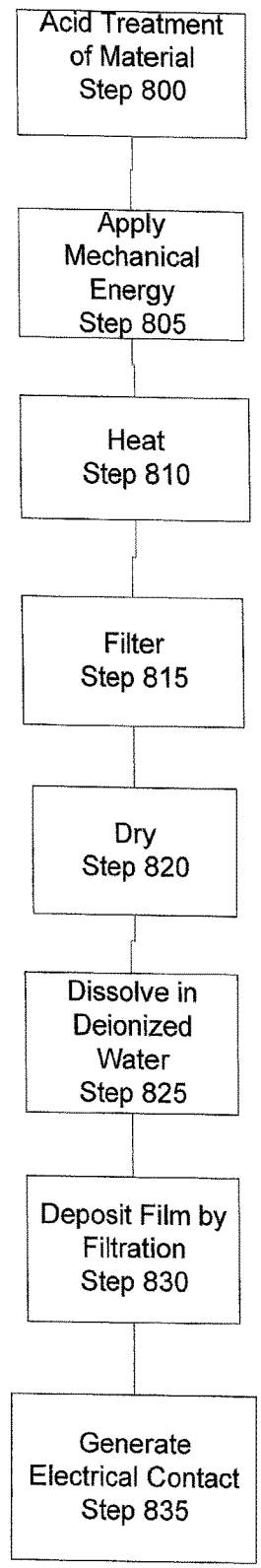
FIG. 8 illustrates an example of a method for forming a CNT condensation sensor.

FIG. 8 illustrates an example of a method for forming the CNT sensor 10.

The CNT sensor can be comprised of single walled carbon nanotubes (SWCNTs), multi-walled carbon nanotubes (MWCNTs), graphene, graphene oxide, or other continuous 2-dimensional conjugated pi-bonded carbon network surface material. In an aspect of the disclosure, the CNT sensor is a multi-walled carbon nanotubes.

The CNT condensation sensor may be composed of a single carbon nanotube (CNT), several carbon nanotubes (CNTs), a random isotropic network of CNTs (random mat or film of CNT), an oriented anisotropic network of CNTs, or multiple of (CNTs) in an oriented bundle. In as aspect of the disclosure, the CNT condensation sensor is composed of at least one CNT randomly deposited as a film.

The CNT sensor may be composed of carbon nanotubes (CNTs) 1 to 100 nanometer (nm) in diameter and 0.1 to 100 microns (μm) in length. In an aspect of the disclosure, the CNT consists of CNTs 10 to 20 nm in diameter and 1 to 10 μm in length.

In an aspect of the disclosure no addition of a secondary binder is used, but rather uses the CNT defect structure itself as a binder and source of dangling carbon chains and moieties for binding along with chemical processing in which thermal and mechanical energy are provided as indicated. Alternatively, the CNT sensor composite can be made from CNTs and an appropriate binder such as a polymer including but not limited to polyethylene, polypropylene, polytetrafluoroethylene, epoxy, cyanoacrylate.

In an aspect of the disclosure, the CNT sensor is formed by chemical activation, followed by chemical, thermal and mechanical processing. At step 800, at least one carbon nanotube is treated with an acid solution. The CNT condensation sensor has a surface chemistry consisting of defects consisting of oxygenated functional surface groups containing, for example (but not limited to), one or more of the following polar carbon-oxygen groups: carboxyl and phenol (phenolic hydroxyl).

Alternatively, the CNT condensation sensor can have a surface chemistry consisting of oxygenated functional surface groups containing, for example (but not limited to), one or more of the following polar carbon-oxygen groups: carboxyl and phenol (phenolic hydroxyl), lactone, lactol, carbonyl, anhydride, ether, and quinine.

For example, the surface chemistry can consist of a mixture of carboxyl, phenolic hydroxyl, lactone, and lactol.

The acid solution can include an oxidant such as hydrogen peroxide, nitric acid, sulfuric acid/nitric acid solution of 10:1 to 1:10 diluted or not diluted in water, or a permanganate oxidizing solution. In as aspect of the disclosure, the acid solution includes a 3:1 concentrated sulfuric acid to concentrated nitric acid solution.

At step 805, a mechanical energy is applied to the treated material (e.g., the dispersion). The mechanical energy can be in the form of mixing and/or ultrasonic energy. For example, the treated material, e.g., dispersion can be connectively stirred using a stifling bar to stir the solution. Alternatively, the mechanical energy can be provided in the form of ultrasonic energy in which the dispersion is sonicated. In an aspect of the disclosure, a combination of convective stirring and sonication is used. For example, the sonication can be employed in the initial stage and stifling being employed in later stage(s).

At step 810, the treated material (e.g., dispersion) is heated, e.g., a thermal energy is applied.

The mechanical processing and thermal processing can be performed simultaneously. The mechanical processing and thermal processing can be performed as series of steps.

First, the treated material (e.g., dispersion) is sonicated without heat for 1 to 24 hours. Afterwards, the treated material (e.g., dispersion) is stirred and heated to a temperature of 45 to 70° C. for another 1 to 24 hours, and then the temperature of the treated material (e.g., dispersion) is decreased to 20 to 40° C. Additionally, the treated material (e.g., dispersion) is stirred for 1 to five days.

At step 815, the treated material (e.g., dispersion), e.g., oxidized CNT-chemical oxidant mixture, is filtered with deionized water (water bath) until the pH of the filtrate is 7 or neutral.

At step 820, the resulting filtered material is oven dried for 1 to 24 hours at a temperature of 70-120° C. to obtain a powder.

At step 825, in order to manufacture a sensor of a certain CNT film thickness, a specified amount of powder is placed in deionized water and filtered through a filter surface which can be easily dissolved in order to get a free-floating film of CNT. The specified amount is determined via a calculation.

The filter can be a 0.1 micron Cellulose Easter Filter. In another aspect of the disclosure, acetone can be used.

At step 830, the free-floating film of CNT previously deposited as a thin film by filtration onto a surface which may be removed or dissolved, is placed or deposited on an insulating dielectric surface. The insulating dielectric surface can be, but is not limited to alumina (aluminum oxide) and silica (silicon dioxide).

At step 835, an electrical contact is made by a conductive composite. The conductive composite can be a silver epoxy. Alternatively, the electrical contact can be made by depositing the CNT thin film onto an insulating dielectric surface where an interdigital conductive pattern of gold, silver, platinum, or other conductive metal has been pre-deposited for making contact to the CNT thin film.

A CNT sensor 10 made by the above process is configured to be sensitive to polar molecules such as water ($H_2O$), ammonia ($NH_3$), or the following chemical groups: alkyl halides, alcohols, aldehydes, ketones, carboxylic acids, amines, esters, and any other polar molecule as determined by its dipole moment in which polar molecules will typically be considered as having a dipole moment of ~0.5 to 3 debye: water (1.85 debye) and ammonia (1.47 debye) for example.

The same is very insensitive to non-polar molecules such as oxygen ($O_2$), nitrogen ($N_2$), hydrogen ($H_2$), carbon dioxide ($CO_2$), and hydrocarbon molecules such as methane ($CH_4$), ethane ($C_2H_6$), propane ($C_3H_8$), and butane ($C_4H_{10}$), extremely sensitive to moisture—as determined by its dipole moment in which non-polar molecules will typically be considered as having a dipole moment of approximately 0 to 0.2 debye.

Further, the CNT sensor 10 made by the above process has a sensitivity that is greatest for polar molecules having large dipole moments greater than about 1.4 debye—water (1.85 debye) and ammonia (1.47 debye) for example—measured in gas streams containing non-polar molecules having dipole moments close to zero—air (0 debye), nitrogen (0 debye), oxygen (O debye), carbon dioxide (0 debye), hydrogen (0 debye), methane (0 debye), ethane (0 debye), ethylene (0 debye), propane (0.08 debye), carbon monoxide (0.11 debye), benzene (0 debye), and others in which the dipole moment is small, typically less than approximately 0.1 debye.

Furthermore, the CNT sensor 10 made by the above process is sensitive to liquid water and solid water (ice); can detect the formation of liquid phase water; and can detect the formation of solid phase water (ice); and can distinguish between liquid water condensation and solid water (ice condensation).

The CNT sensor 10 is also configured to measure the dew point of polar molecules in a gas mixture where the other constituents are non-polar molecules. Additionally, the CNT sensor 10 is also configured to measure the dew point of a target polar molecule in a background gas stream consisting of nonpolar molecules and polar molecules in which the dew point of the background polar molecules is lower than the dew point of the target polar molecule.

The CNT sensor 10 made by the above process can:
detect the dew point of water ($H_2O$) in non-polar inorganic gas streams such as oxygen, nitrogen, air, hydrogen, helium, argon, sulfur hexafluoride, and silane;
detect the dew point of water in carbon dioxide, a gas which reacts with water to form carbonic acid; and
detect the dew point of water in hydrocarbon streams such as methane, ethane, ethylene, propane, butane, pentane, hexane, heptane, octane, benzene, and other hydrocarbons with small dipole moments.

Prior to measurement, the CNT sensor 10 is heated to clean condensation, e.g., liquid or solid, on the surface. The processor 35 may also be configured to measure the CNT sensor resistance prior to a temperature scan. For example, the processor may measure the CNT sensor resistance at a temperature between 20-30 degrees C. This measurement can be used to estimate the dew point. This estimation allows for the dew point to be classified into a range, such as between −40 degrees C. and 20 degrees C. or less than −40 degrees C.

EXPERIMENTAL RESULTS

A CNT sensor 10 formed by the above-identified method was tested using both a slow scan rate and a fast scan rate using a known humidity level in a gas. The fast scan rate was performed using a modified commercial thermoelectric three stage cooling Peltier cell. The slow scan rate was performed using cryogenic cooling.

A four channel Bubbler was used to generate a gas flow with a known humidity level. One channel was the source of the gas. In the experiment, the gas was Nitrogen. The other three channels contained different levels for humidity. The humidity of the gas was controlled using one or more of the three channels.

Figure 9:
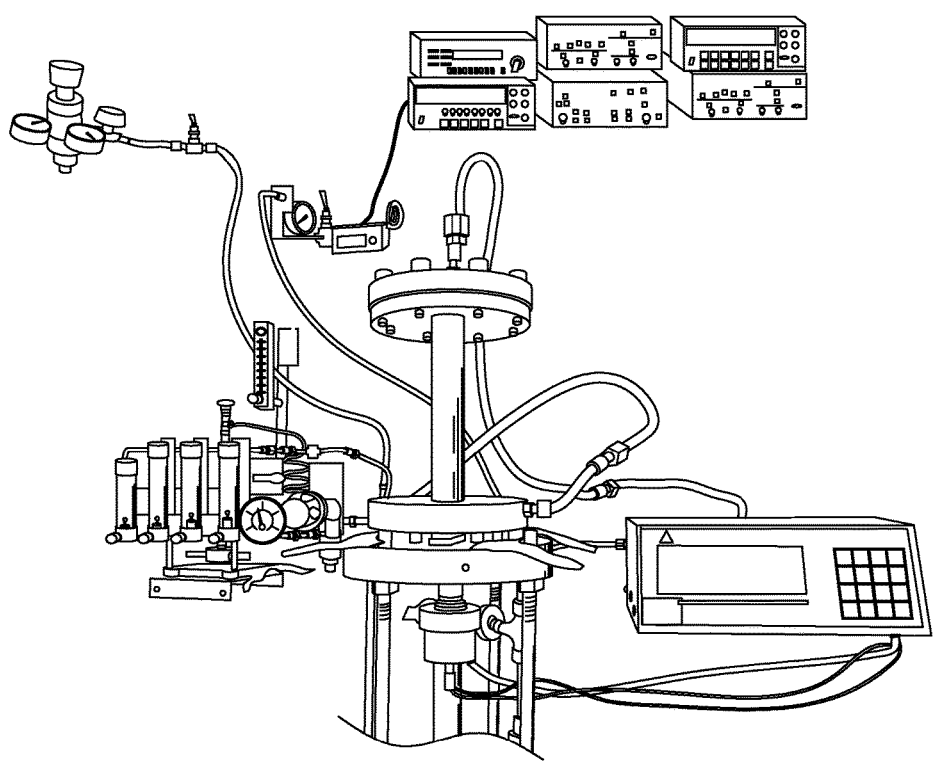
FIG. 9 illustrates a photograph of a general view of an experimental setup.

FIG. 9 illustrates a photograph of the experiment setup. The modified DewMaster (Serial No. 37457, Edgetech) is depicted on the right hand side. The cryogenic cooling cell is depicted on the floor in the center of the photograph. The four channel Bubbler (Dewpoint generator-SPECIAL, part number: DG0.00A1000, by COSA Xentaur Corporation) is depicted in the left of the photograph on the test bench. A processor for analysis the experimental data is not shown.

Figure 10:
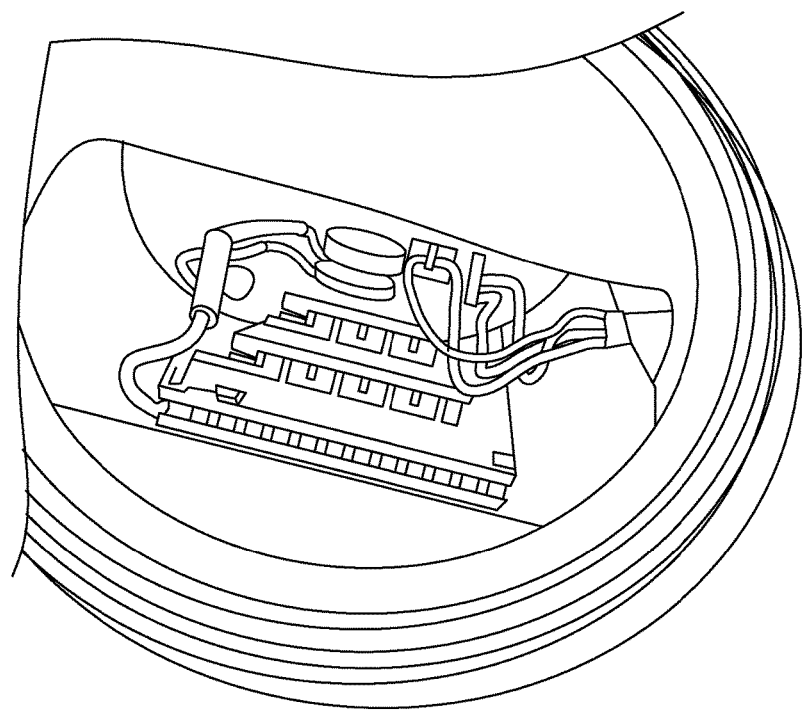
FIG. 10 illustrates a photograph of a portion of a modified commercial DewMaster with a CNT sensor, temperature sensor and three stage Peltier cell.

FIG. 10 illustrates a photograph of a modified portion of the Dewmaster (inside). The three stage Peltier cell is depicted in the center of the photograph. Both the CNT sensor 10 and temperature sensor 5 are located by the chilled mirror on the top of the third stage of the Peltier cell. The temperature sensor in the experiment was a Pt RTD.

On the right of the temperature sensor 5 and CNT sensor 10 are four white wires, two each for the temperature sensor 5 and CNT sensor 10, respectively. The wires are coupled to the processor (not shown) for processing the output of the temperature sensor 5 and CNT sensor 10.

Figure 11:
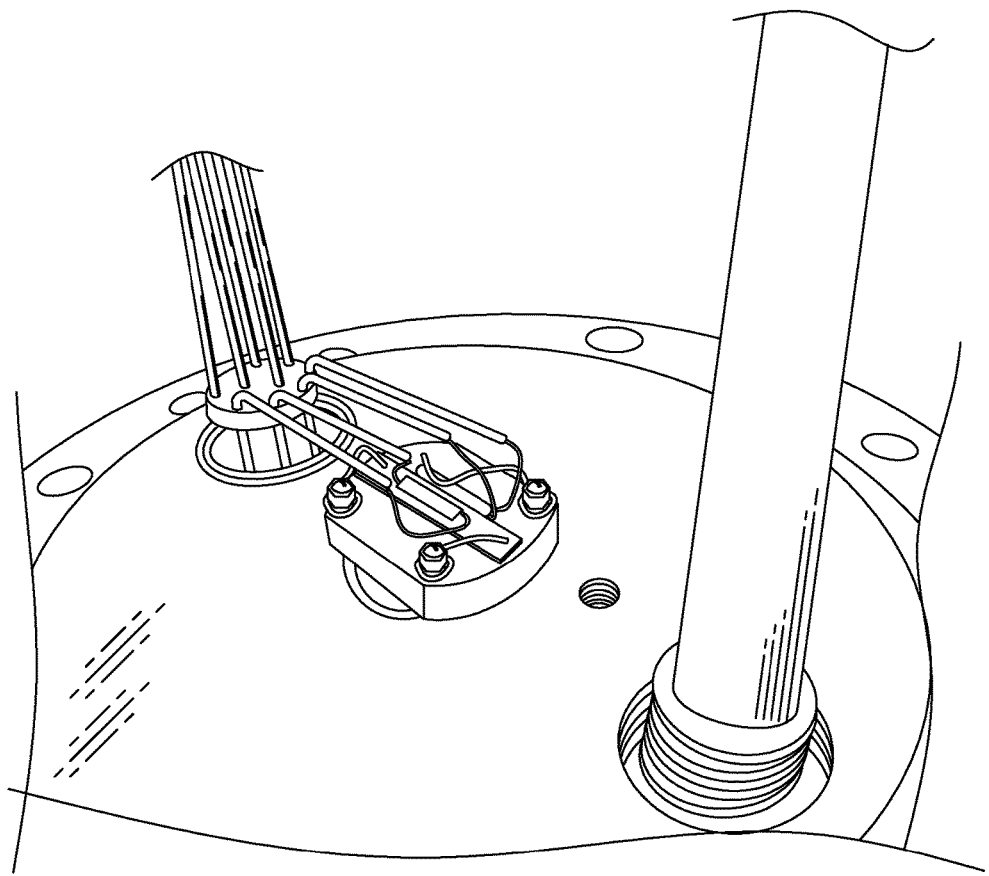
FIG. 11 illustrates a photograph of a portion of a cryogenic cooling cell having the CNT sensor, temperature sensor and control humidity sensor.

FIG. 11 illustrates a photograph of the sensing portion used in conjunction with the cryogenic cooling.

The CNT sensor 10 and Pt RTD sensor, e.g., temperature sensor are located on the top of a small Cu table (center of photograph), which is thermally connected to liquid N2 reservoir. A control LPDT sensor is mounted nearby. The CNT sensor 10 appears in the photograph diagonally (on the center of the CU table). The Pt RTD sensor is located at the right side of the CNT sensor 5. Wires similarly couple the sensors with the processor.

Figure 12:
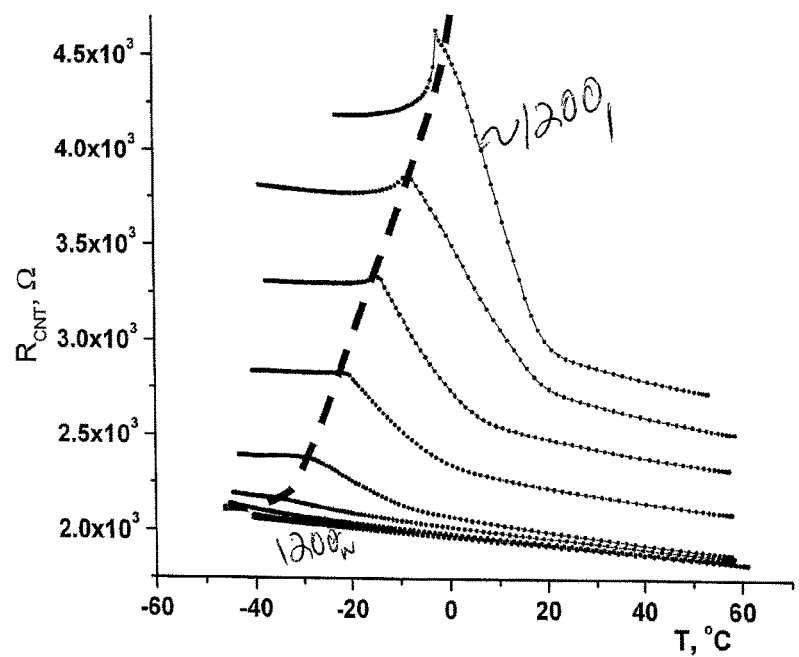
FIG. 12 illustrates various resistance of the CNT condensation sensor verses temperature curves for different humidity levels.

FIG. 12 illustrates various resistance of the CNT sensor verses temperature curves for different humidity levels. As can be seen from FIG. 12, if the temperature drops down, significant resistance increase takes place while condensation occurs, following by the max point of the resistance and sudden resistance drop due to the ice formation. These points correspond to the Frost point. The dashed line intersects the frost point for each curve. Depending on the humidity level, the steepness of the slope before the peak changes, e.g., difference between $1200_1$ verses $1200_n$.

Figure 13:
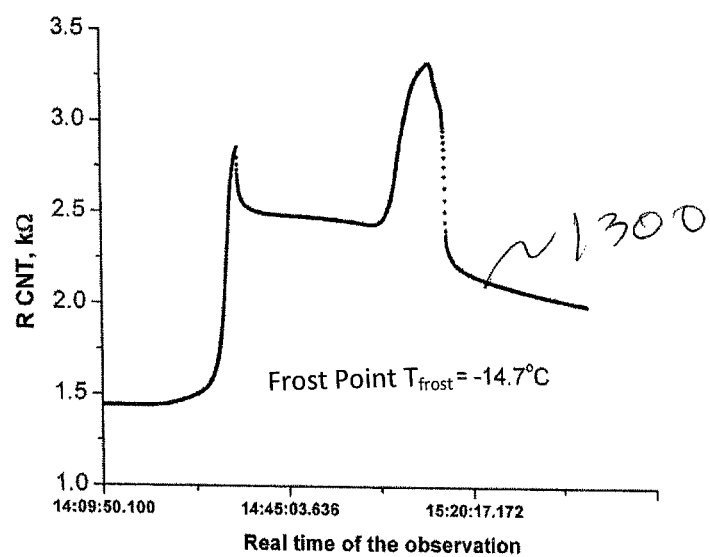
FIG. 13 illustrates a single curve of the resistance of the CNT condensation sensor over a time (and temperature) of observation for a slow scan.

FIG. 13 illustrates a single curve of the resistance of the CNT sensor 130 over a time of observation for a slow scan. The curve represents a temperature change from a high temperature to a low temperature and back from a low temperature to a high temperature. This is the reason why the curve exhibits two peaks.

Slow temperature scans made in the cryo-cell result in very distinct peaks. The first peak represents the change in state as the temperature was slowly decreased; whereas the second peak, which is wider, represents the change in state as the temperature was slowly increased. The frost point $T_{frost}$ was determined to be −14.7° C.

Figure 14:
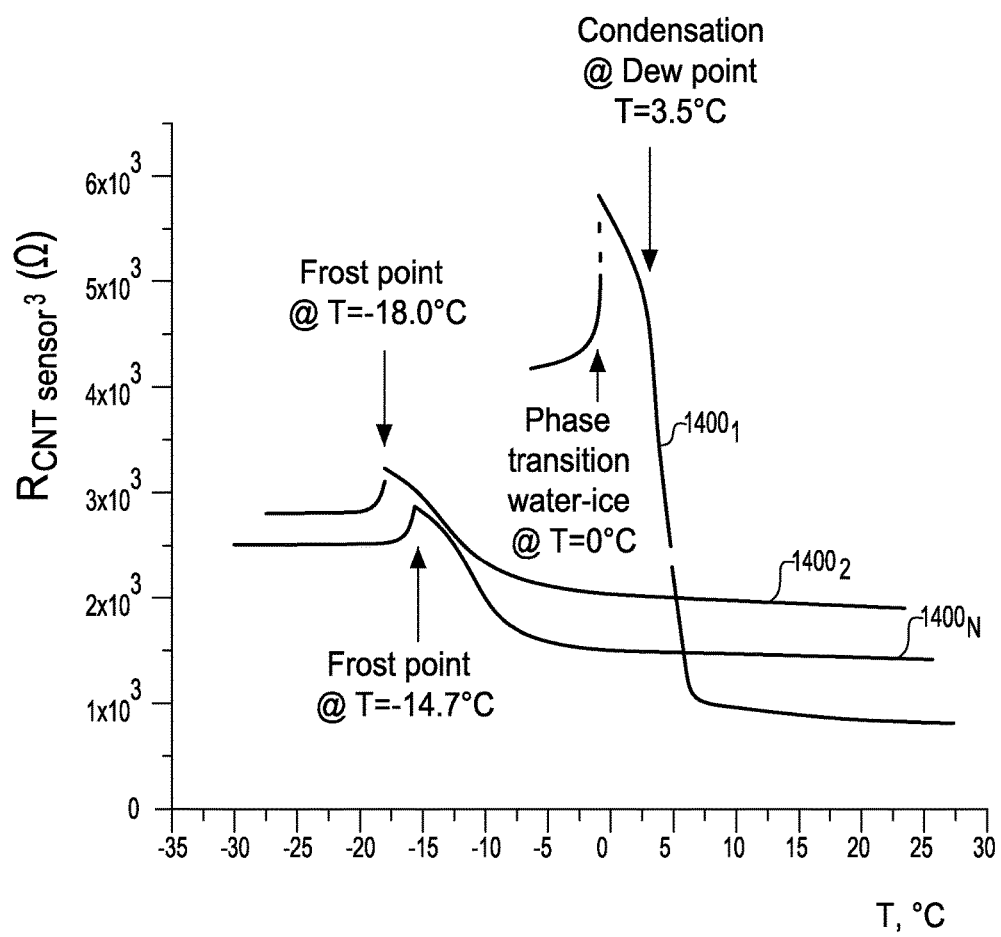
FIG. 14 illustrates three curves of the resistance of the CNT condensation sensor detected as the temperature was slowly decreased where the humidity in the gas had three different levels.

FIG. 14 illustrates three curves of the resistance of the CNT sensor $1400_{1-N}$ detected as the temperature was slowly decreased where the humidity in the gas had three different levels. The arrowed lines indicate the dew points determined based on the respective curves.

As noted earlier, as control sensor was used to determine the accuracy of the CNT sensor 10. In the experiment, a Loop Power Dewpoint Transmitter (LPDT) was used.

Figure 15:
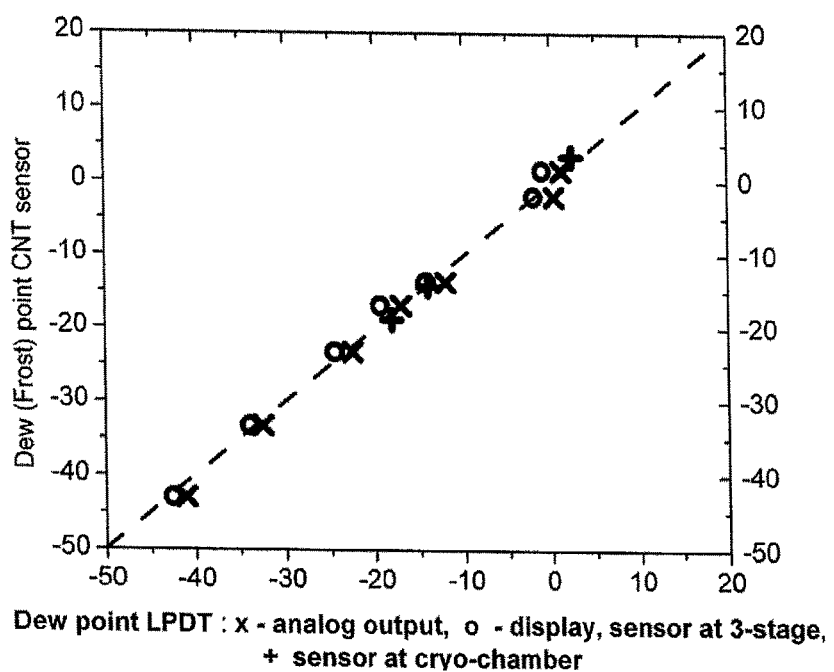
FIG. 15 illustrates the relationship between the results from the fast and slow scans in respect to LPDT measurements.

FIG. 15 illustrates the relationship between the results from the fast and slow scans with respect to the LPDT measurements.

The points labeled "O" represent data from the fast scan and the points labeled "+" represent data from the slow scan and points labeled "x" represent data from the LPDT. As can be seen from the figure, the fast and slow scans are close to the LPDT measurements.

Figure 16:
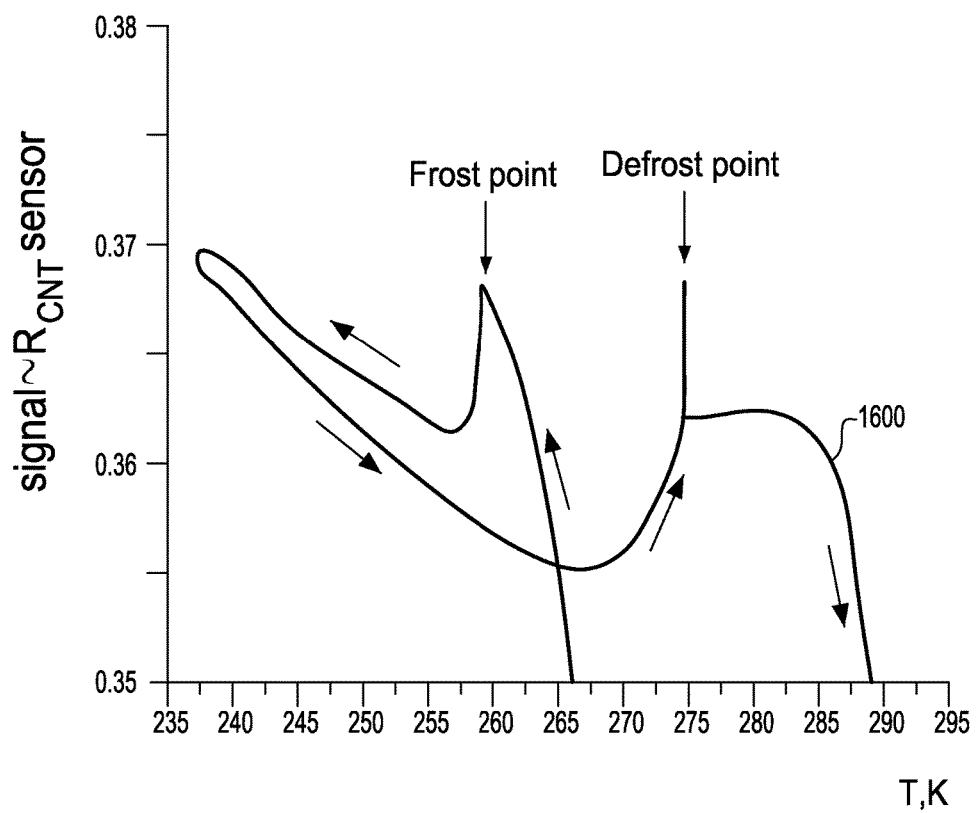
FIG. 16 illustrates a curve of the output signal voltage across CNT condensation sensor which is proportional to the resistance of the CNT condensation sensor verses temperature in Kelvin for an additional example of a slow scan.

FIG. 16 illustrates a curve of the output signal voltage across the CNT sensor which is proportional to the resistance of the CNT sensor. The curve is verses temperature in Kelvin for another slow scan 1600. The arrows indicate the direction of the change in temperature. First the temperature was decreased from a high temperature to a low temperature. Then, the temperature was increased from the low temperature to the high temperature which is the reason why there are two observed peaks. The Frost point is identified by an arrow. The defrost point is identified by a second arrow. The peaks are shifted with respect to each other due to the difference between $T_{frost}$ and ice melting ($T_{ice}$).

Figure 17:
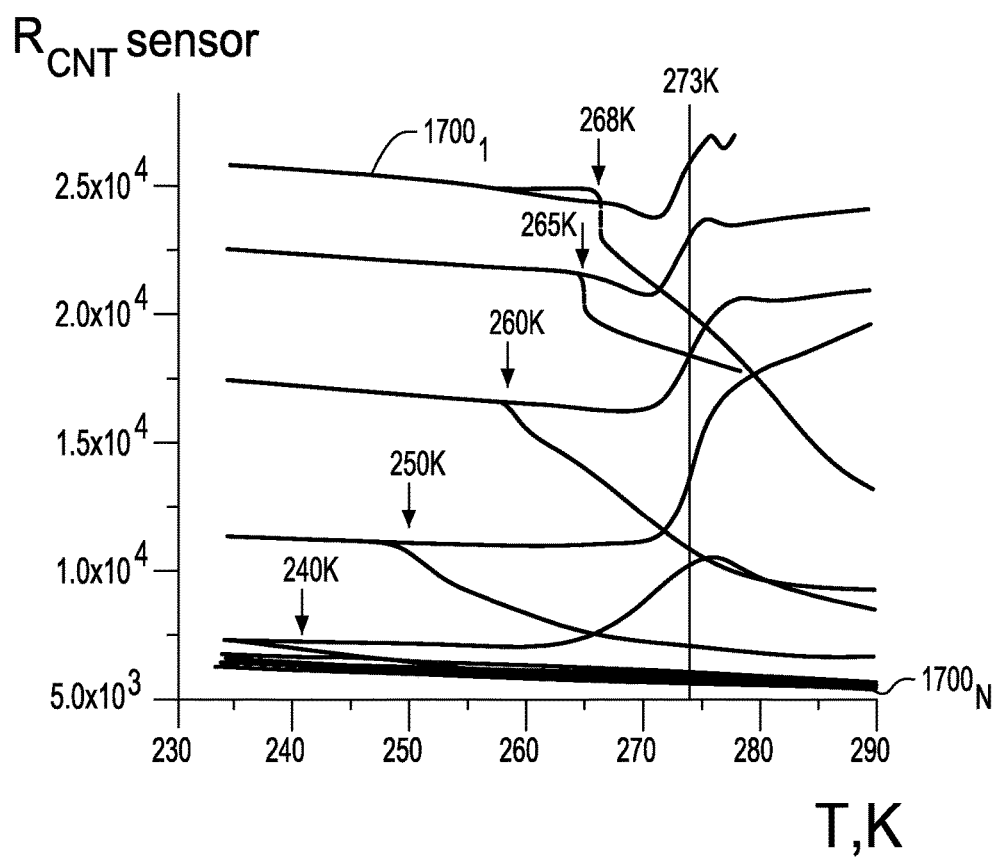
FIG. 17 illustrates results from additional examples of fast scans of gases with different humidity levels verses the scanned temperature.

FIG. 17 illustrates results $1700_{1-N}$ from other fast scans of gases with different humidity levels verses the scanned temperature. The Frost points for each respective curve are identified with arrows (and numbers above the arrows). The vertical line represents the melting point of ice in which ice forms liquid water which eventually evaporates from the surface. The temperature is 273K.

Figure 18:
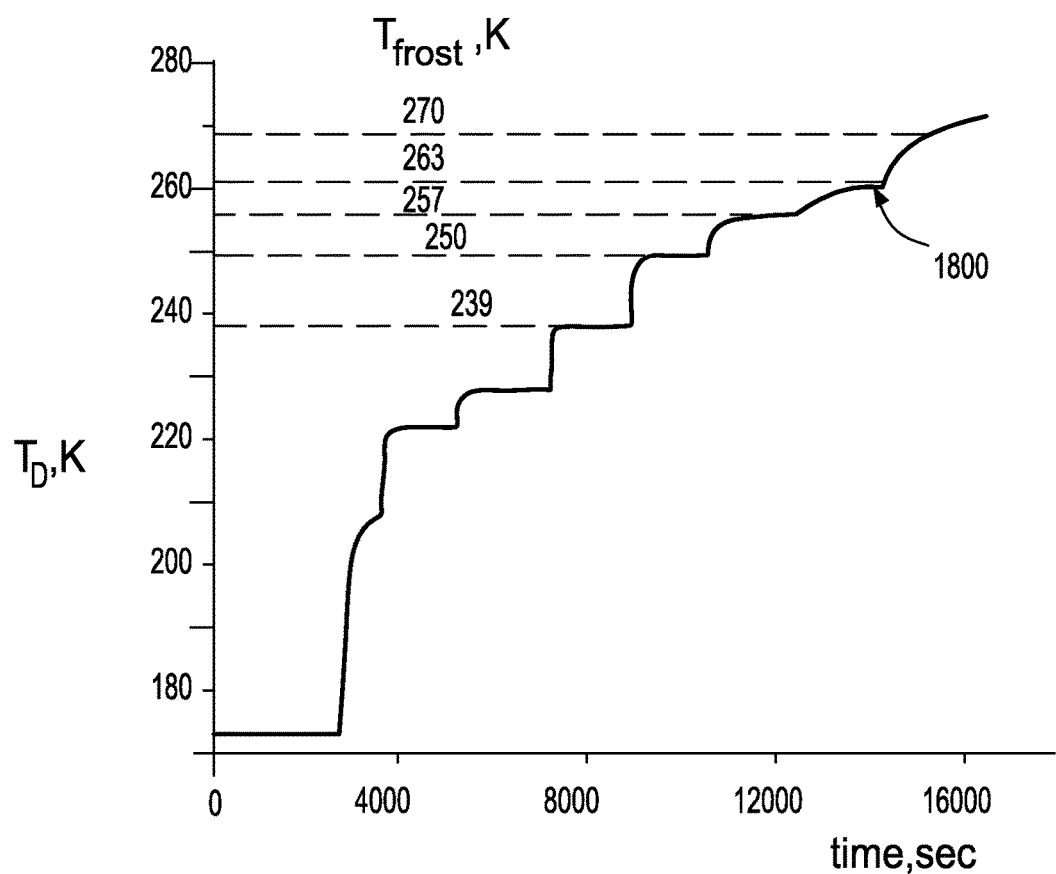
FIG. 18 illustrates a $T_{frost}$ in Kelvin over a time of another scan example.

The humidity was gradually increases over time. The resistance 1800 of the CNT sensor was observes during a plateau, e.g., when the humidity stabilized. FIG. 18 illustrates the $T_{frost}$ in Kelvin over the time of the scan.

Figure 19:
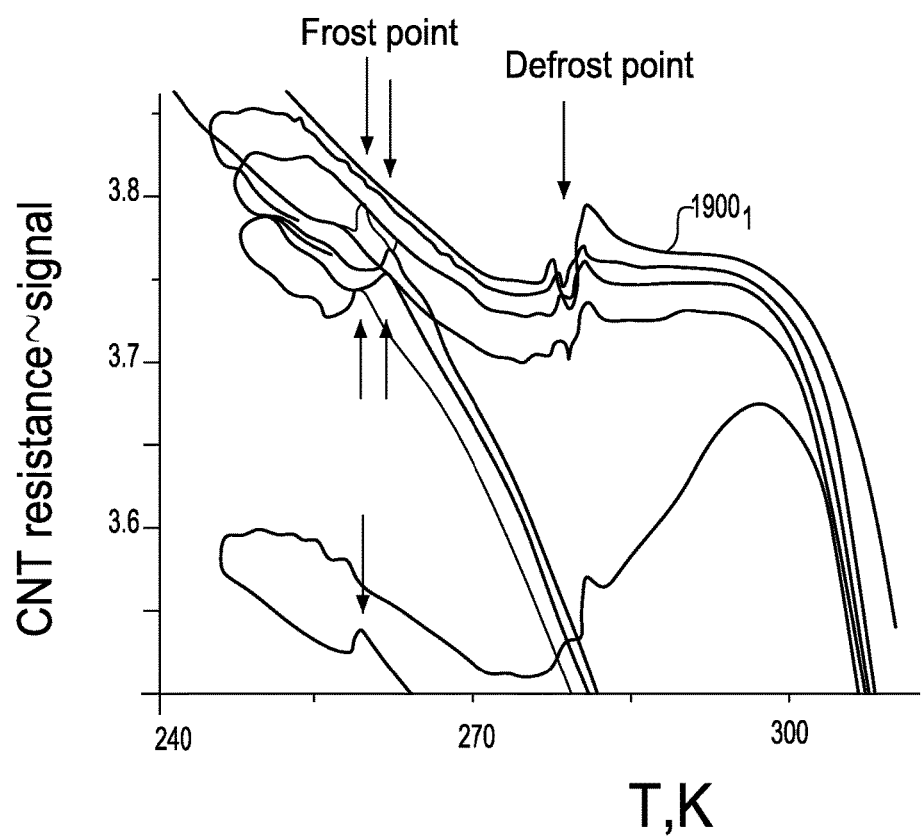
FIG. 19 illustrates results of examples of fast scans which repeated the fast scan for five successive times as the same $T_{frost}$ value.

The scans can be repeated. FIG. 19 illustrates the results of repeating a fast scan for five successive times $1900_{1-N}$. FIG. 19 only depicts the temperature range(s) near the frost and defrost points rather than the full scan for illustrative purposes. As can be seen from FIG. 19, the frost point $T_{frost}$ changes slights for the different scans, but the defrost point is the same. The reason is that the defrost point represents the conversion of ice or frost on the CNT sensor 10 which melts at 273K forming water which eventually evaporates from the CNT sensor 10 as the temperature is raised and it dries. In contrast, the frost point, is a point during the cooling of the surface of the CNT sensor 10 on which the first frost or ice starts to form. Because it is not at equilibrium, the temperature is based on the humidity of the gas steam, e.g., the concentration of water vapor present in the gas.

The above experiment uses Nitrogen as the base gas. However, a CNT sensor 10 can be used to determine the dew point in other gases.

Figure 20A:
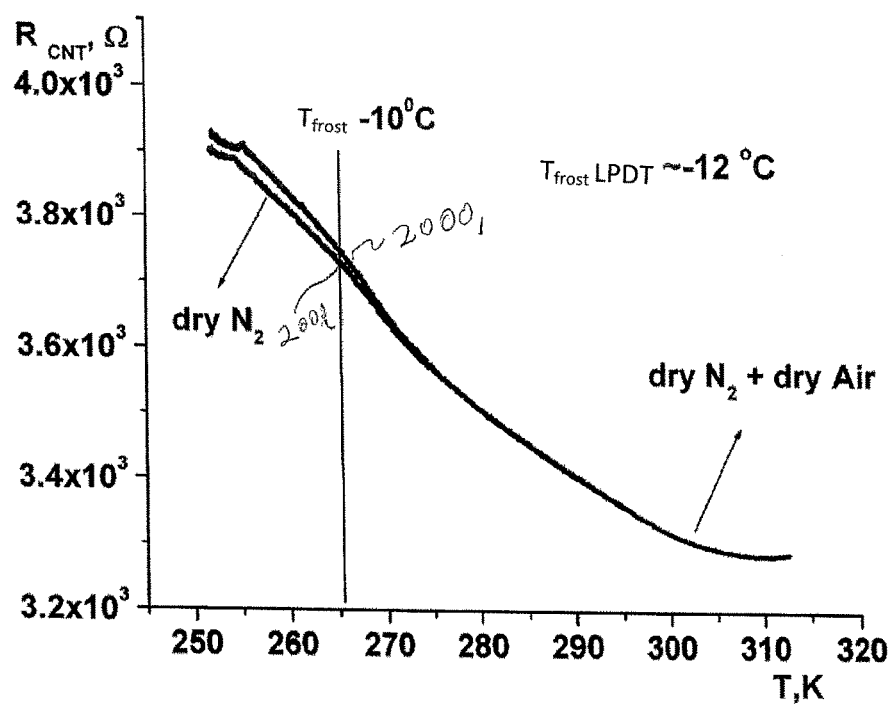
FIGS. 20A and 20B depict resistance curves for a CNT sensor in accordance with aspects of the disclosure measuring a frost point or dew point for dry $N_2$ and Dry Air in comparison with just dry $N_2$.
Figure 20B:
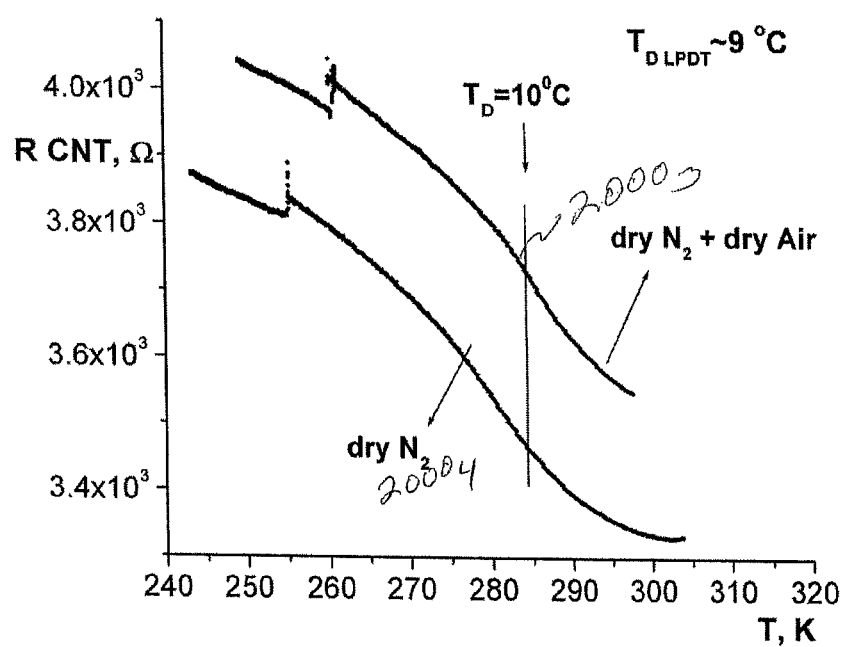

FIGS. 20A and 20B depict resistance curves for the CNT sensor measuring a frost point or a dew point for dry $N_2$ and Dry Air $2000_1$ in comparison with just dry $N_2$ $2000_2$. FIG. 20A shows curves for a low frost points. FIG. 20B shows the curves for a high dew point. The curves in FIGS. 20A and 20B were generated based on a fast scan. The LPDT was used also for comparing results. The two curves: one for the combination of dry $N_2$ and dry Air $2000_3$ and one for just the dry $N_2$ $2000_4$ show a good correlation. The vertical line indicates the frost point ($T_{frost}$) determined from the CNT sensor. As shown in FIG. 20A, the determined frost point using the CNT sensor was approximately −10° C., whereas the output of the LPDT determined the frost point to be approximately −12° C. The difference in the output of the LPDT and CNT sensor may be attributed to the different locations of the sensors, difference in temperatures and humidity levels in the locations, pressure variations and fluctuations.

For the higher dew point, the two curves show similar slopes, but have different resistance values. The vertical line indicates the dew point ($T_D$) determined from the CNT sensor. As shown in FIG. 20B, the determined dew point using the CNT sensor was approximately 10° C., whereas the output of the LPDT determined the dew point to be approximately −9° C. The x-axis in both FIGS. 20A and 20B is in Kelvin.

The CNT sensor can be used to determine the dew point in $CO_2$.

Figure 21A:
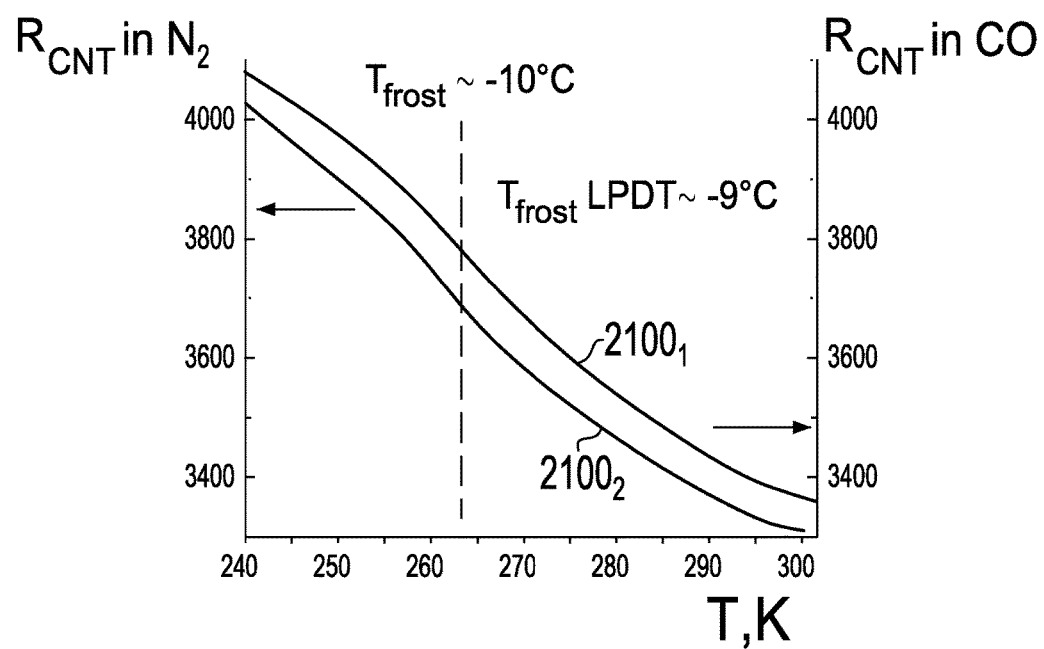
FIGS. 21A and 21B depict resistance curves for a CNT sensor in accordance with aspects of the disclosure measuring frost point or dew point for $N_2$ in comparison with $CO_2$.
Figure 21B:
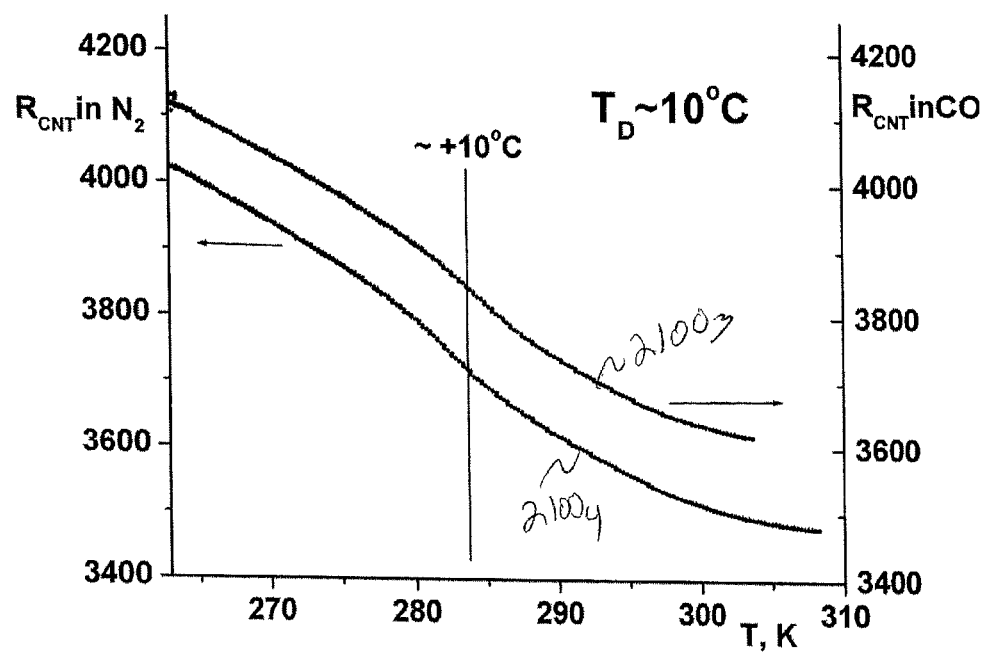

FIGS. 21A and 21B depict resistance curves for the CNT sensor measuring a frost point or a dew point for $N_2$ in comparison with $CO_2$ $2100_{1-4}$. FIG. 21A shows curves for a low frost point ($2100_{1-2}$). FIG. 21B shows the curves for a high dew point $2100_{3-4}$. High scan rates were used to generate the curves. The y-axis for the left side represents the resistance values for the CNT sensor 10 detected for $N_2$. The y-axis for the right side represents the resistance values for the CNT sensor 10 detected for $CO_2$. The x-axis in both FIGS. 21A and 21B is in Kelvin. The vertical line on both figures indicate the frost point/dew point $T_{frost}/T_D$ determined from the CNT sensor, e.g., approximately −10 and 10° C., respectively. In FIG. 21A, the LPDT determined the frost point to be approximately −9° C. In FIG. 21B, the LPDT determined the dew point to be approximately 10° C.

Carbon dioxide is a non-polar gas, which is reactive with water to form carbonic acid, has a triple point @ 5.11 atm of −56.6° C., and a sublimation point @ 1 atm of −78.5° C. As a non-polar gas, the CNT condensation will not be sensitive to it; however, below the triple point listed above, condensation can occur that would block the surface to water diffusion and adsorption and below the sublimation point solid carbon dioxide depositing and covering the surface can occur. An operation at 1 atm, allows for an operation down to −78.5° C. before consideration of its presence is needed. For lower dew points, a fast scan can be used in the dew point determination.

Figure 22A:
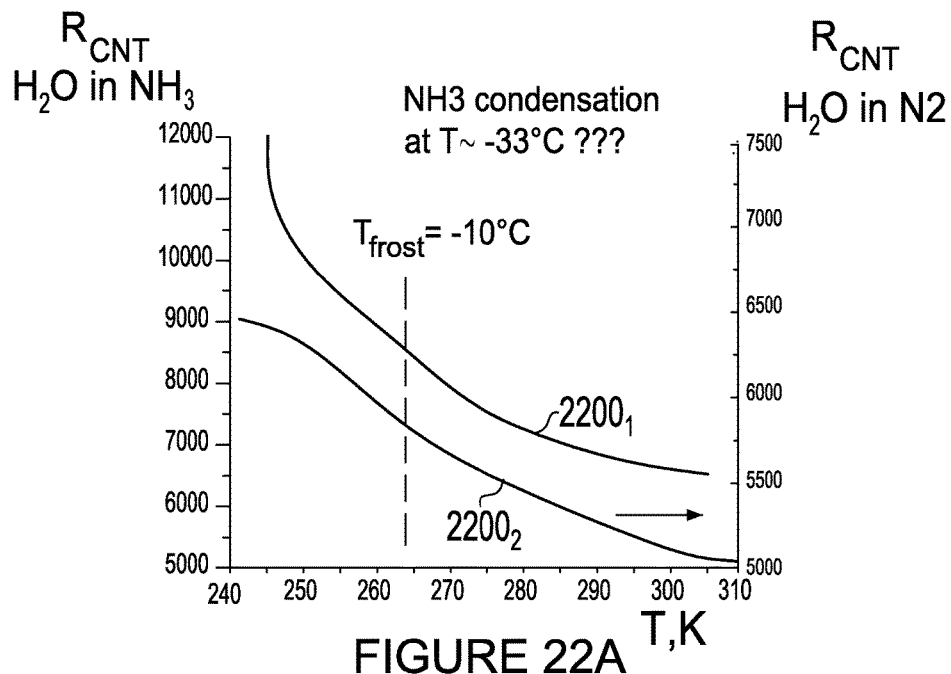
FIGS. 22A and 22B depict resistance curves for a CNT sensor in accordance with aspects of the disclosure measuring frost point or dew point for $H_2O$ in $NH_3$ in comparison with $H_2O$ in $N_2$.
Figure 22B:
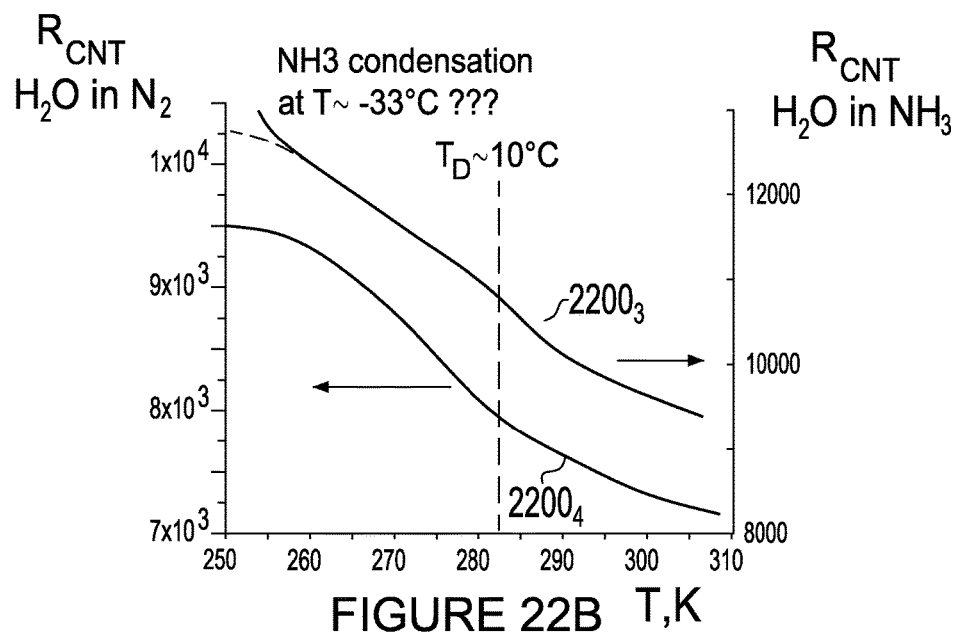

FIGS. 22A and 22B depict resistance curves for the CNT sensor measuring frost point or dew point for $H_2O$ in $NH_3$ in comparison with $H_2O$ in $N_2$ $2200_{1-4}$. FIG. 22A shows curves for a low frost point. FIG. 22B shows the curves for a high dew point. The curves were generated using a fast scan rate. The y-axis for the left side represents the resistance values for the CNT sensor 10 detected for $H_2O$ in $NH_3$. The y-axis for the right side represents the resistance values for the CNT sensor 10 detected for $H_2O$ in $N_2$. The x-axis in both FIGS. 21A and 21B is in Kelvin. The vertical line on both figures indicates the frost point/dew point $T_{frost}/T_D$ determined from the CNT sensor, e.g., −10 and 10° C., respectively.

Ammonia has a boiling temperature of '33.34° C. Ammonia is also a polar gas, which is reactive with water to form a weak basic solution of ammonium hydroxide. Ammonia has a dipole moment of 1.43 D. Water has a dipole moment of 1.85 D.

Pure ammonia has a dew point of about −33.3° C. The dew point of ammonia or ammonia at a lower concentration in a gas matrix can be determined by the CNT sensor by fast scanning of temperature. At low water concentration, an estimate of the dew point can be done by fast scanning of the temperature because the baseline shifts can be ignored, as long as the inflections indicated by slope and changes in slopes due to phase inflections occurring can be determined. If there is sufficient difference in the ammonia dew point and the water dew point, then the inflections can be determined. As depicted in FIGS. 22A and 22B the dew points were sufficient different and therefore, the inflection points can be determined.

Various aspects of the present disclosure may be embodied as a program, software, or computer instructions embodied or stored in a computer or machine usable or readable medium, or a group of media which causes the computer or machine to perform the steps of the method when executed on the computer, processor, and/or machine. A program storage device readable by a machine, e.g., a computer readable medium, tangibly embodying a program of instructions executable by the machine to perform various functionalities and methods described in the present disclosure is also provided, e.g., a computer program product.

The computer medium could be a computer readable storage device or a computer readable signal medium. A computer readable storage device, may be, for example, a magnetic, optical, electronic, electromagnetic, infrared, or semiconductor system, apparatus, or device, or any suitable combination of the foregoing; however, the computer readable storage device is not limited to these examples except a computer readable storage device excludes computer readable signal medium. Additional examples of the computer readable storage device can include: a portable computer diskette, a hard disk, a magnetic storage device, a portable compact disc read-only memory (CD-ROM), a random access memory (RAM), a read-only memory (ROM), an erasable programmable read-only memory (EPROM or Flash memory), an optical storage device, or any appropriate combination of the foregoing; however, the computer readable storage device is also not limited to these examples. Any tangible medium that can contain, or store, a program for use by or in connection with an instruction execution system, apparatus, or device could be a computer readable storage device.

A computer readable signal medium may include a propagated data signal with computer readable program code embodied therein, such as, but not limited to, in baseband or as part of a carrier wave. A propagated signal may take any of a plurality of forms, including, but not limited to, electro-magnetic, optical, or any suitable combination thereof. A computer readable signal medium may be any computer readable medium (exclusive of computer readable storage device) that can communicate, propagate, or transport a program for use by or in connection with a system, apparatus, or device. Program code embodied on a computer readable signal medium may be transmitted using any appropriate medium, including but not limited to wireless, wired, optical fiber cable, RF, etc., or any suitable combination of the foregoing.

The terms "processor" and "temperature controller" as may be used in the present disclosure may include a variety of combinations of fixed and/or portable computer hardware, software, peripherals, and storage devices. The "processor" and "temperature controller" may include a plurality of individual components that are networked or otherwise linked to perform collaboratively, or may include one or more stand-alone components. The hardware and software components of the "processor" and "temperature controller" of the present disclosure may include and may be included within fixed and portable devices such as desktop, laptop, and/or server, and network of servers (cloud).

The terminology used herein is for the purpose of describing particular embodiments only and is not intended to be limiting the scope of the disclosure and is not intended to be exhaustive. Many modifications and variations will be apparent to those of ordinary skill in the art without departing from the scope and spirit of the disclosure.

What is claimed is:

1. A system comprising:
  a carbon nanotube (CNT) condensation sensor having a moisture sensitive resistance, where a current is supplied to the CNT condensation sensor from a current source and where a voltage across the CNT condensation sensor is detected;
  a thermal device configured to generate heating or cooling to change a temperature of the CNT condensation sensor;
  a temperature sensor for measuring a temperature of the CNT condensation sensor;
  a controller configured to control the thermal device; and
  a processor configured to determine one or more parameters based on the moisture sensitive resistance determined from the supplied current and the detected voltage of the CNT condensation sensor and the temperature measured by the temperature sensor, the temperature measured being a result of the controlled heating or cooling generated by the thermal device.

2. The system of claim 1, wherein the controller is configured to control a temperature scan rate of the thermal device.

3. The system of claim 2, wherein the temperature scan rate is between about 0.001° C./sec and about 10° C./sec.

4. The system of claim 2, wherein the temperature scan rate includes a fast temperature scan rate of between about 0.1 and about 10° C./sec.

5. The system of claim 4, wherein the temperature scan rate includes a slow temperature scan rate of between about 0.001 and about 0.1° C./sec.

6. The system of claim 5, wherein the controller is configured to switch between the fast temperature scan rate and the temperature slow scan rate.

7. The system of claim 1, wherein the thermal device is a multi-stage thermoelectric device.

8. The system of claim 1, further comprising a current source coupled to the temperature sensor and to the CNT condensation sensor; and voltage detector configured to detect voltage across the temperature sensor and the CNT condensation sensor, the detected voltages being proportional to a resistance of the temperature sensor and the moisture sensitive resistance of the CNT condensation sensor.

9. The system of claim 1, wherein the processor is configured to determine the one or more parameters based on analyzing the moisture sensitive resistance over time.

10. The system of claim 9, wherein the one or more parameters being selected from a group consisting of maximum resistance point with respect to temperature, a first derivative of resistance with respect to temperature and a second derivative of resistance with respect to temperature.

11. The system of claim 10, wherein the processor is configured to determine a dew point based on at least one of the one or more parameters.

12. The system of claim 11, wherein when the dew point is greater than 0(° C.), a $T_{inflection}$ (° C.) is the dew point, where $T_{inflection}$ is a temperature where: 1) the first derivative is a minimum, 2) the first derivative is less than 0 for both $T>T_{inflection}$ and $T<T_{inflection}$, 3) the second derivative equals 0 and 4) the second derivative is greater than 0 for surface temperatures $T_{surface}$ (° C.) above $L_{inflection}$ (° C.) and the second derivative is less than 0 for surface temperatures $T_{surface}$ (° C.) below $T_{inflection}$ (° C.).

13. The system of claim 11, wherein when the dew point is less than 0(° C.), the dew point is determined based on a frost point, $T_{frost}$, when no $T_{inflection}$ is detected, where $T_{frost}=T_{ice}$, where $T_{ice}$ a temperature where: 1) the first derivative is less than 0 for $T_{surface}$ (° C.)>$T_{ice}$ (° C.), 2) the first derivative is greater than 0 for T (° C.)<$T_{ice}$ (° C.), 3) the first derivative is equal to 0 at $T_{ice}$ (° C.) or T) or the first derivative is undefined at $T_{ice}$ (° C.), 4) conditions 1-3 resulting in a maximum extremum or "peak" in the $R_{cnt}$ (ohms) versus $T_{surface}$ (° C.) curve where $T_{surface}$ (° C.) equals $T_{ice}$ (° C.), and 5) immediately following $T_{ice}$ (° C.), as the surface temperature is further decreased, a magnitude of the moisture sensitive resistance $R_{CNT}$ drops off abruptly in magnitude providing a characteristic icing signature.

14. A method comprising:
controlling a temperature of a carbon nanotube (CNT) condensation sensor, the temperature is controlled to start at a maximum temperature, the maximum temperature being higher than an expected dew point, the controlling the temperature including decreasing the temperature at a controllable scan rate;
supplying a current to the CNT condensation sensor from a current source;
detecting, continuously a voltage across the CNT condensation sensor over time;
detecting, continuously a voltage across a temperature sensor over time, the temperature sensor disposed near the CNT condensation sensor;
calculating moisture sensitive resistance of the CNT condensation sensor from the continuously detected voltage across the CNT condensation sensor and the supplied current; and
determining one or more parameters based on the moisture sensitive resistance and the temperature.

15. The method of claim 14, wherein the one or more parameters being selected from a group consisting of maximum resistance point with respect to temperature, a first derivative of resistance with respect to temperature and a second derivative of resistance with respect to temperature.

16. The method of claim 15, further comprising:
determining an ice point temperature $T_{ice}$ based the one or more parameters.

17. The method of claim 16, wherein the decrease in the temperature of the surface is stopped at the $T_{ice}$.

18. The method of claim 17, wherein the controlling of the temperature of a surface, further including increasing the temperature of the surface to the maximum temperature when the $T_{ice}$ is reached.

19. The method of claim 16, wherein the $T_{ice}$ is where: 1) the first derivative is less than 0 for $T_{surface}$ (° C.)>$T_{ice}$ (° C.), 2) the first derivative is greater than 0 for T (° C.)<$T_{ice}$ (° C.), 3) the first derivative is equal to 0 at $T_{ice}$ (° C.) or the first derivative is undefined at $T_{ice}$ (° C.), 4) conditions 1-3 resulting in a maximum extremum or "peak" in the $R_{cnt}$ (ohms) versus $T_{surface}$ (° C.) curve where $T_{surface}$ (° C.) equals $T_{ice}$ (° C.), and 5) immediately following $T_{ice}$ (° C.), as the surface temperature is further decreased, a magnitude of the moisture sensitive resistance $R_{CNT}$ drops off abruptly in magnitude providing a characteristic icing signature.

20. The method of claim 16, further comprising:
detecting an inflection point temperature $T_{inflection}$ based the one or more parameters.

21. The method of claim 20, wherein $T_{inflection}$ is a temperature where: 1) the first derivative is a minimum, 2) the first derivative is less than 0 for both $T>T_{inflection}$, inflection and $T<T_{inflection}$, 3) the second derivative equals 0 and 4) the second derivative is greater than 0 for surface temperatures $T_{surface}$ (° C.) above $T_{inflection}$ (° C.) and the second derivative is less than 0 for surface temperatures $T_{surface}$ (° C.) below $T_{inflection}$ (° C.).

22. The method of claim 21, further comprising:
determining a dew point temperature $T_{dew}$.

23. The method of claim 22, wherein when $T_{inflection}$ is greater than 0, $T_{dew}=T_{inflection}$.

24. The method of claim 22, wherein when $T_{inflection}$ is less than 0, $T_{dew}$ is determined based on a frost point $T_{frost}$.

25. The method of claim 21, wherein the method detects the $T_{dew}$ of polar molecules in a gas mixture.

26. The method of claim 25, wherein the gas mixture includes components selected from a group consisting of oxygen ($O_2$), nitrogen ($N_2$), hydrogen ($H_2$), carbon dioxide ($CO_2$), and hydrocarbon molecules such as methane ($CH_4$), ethane ($C_2H_6$), propane ($C_3H_8$), and butane ($C_4H_{10}$).

27. The method of claim 25, wherein the polar molecules are selected from a group consisting of water and ammonia.

28. The method of claim 21, wherein the method detects the $T_{dew}$ of a target polar molecule in a background gas stream consisting of nonpolar molecules and polar molecules in which the dew point of the background polar molecules is lower than the dew point of the target polar molecule.

\* \* \* \* \*